(12) United States Patent
Sancho Durá et al.

(10) Patent No.: US 12,011,218 B2
(45) Date of Patent: Jun. 18, 2024

(54) METHODS, DEVICES, AND SUPPORT STRUCTURES FOR ASSEMBLING OPTICAL FIBERS IN CATHETER TIPS

(71) Applicant: Medlumics S.L., Madrid (ES)

(72) Inventors: Juan Sancho Durá, Tres Cantos (ES); Sara Mas Gómez, Tres Cantos (ES); David Gonzalez, Alcobendas (ES); Matthieu Duperron, Madrid (ES); Carlos Sanz Moreno, Barajas (ES); Jorge Jimenez, Atlanta, GA (US); Alexandre Romoscanu, Geneva (CH)

(73) Assignee: Medlumics S.L., Madrid (ES)

( * ) Notice: Subject to any disclaimer, the term of this patent is extended or adjusted under 35 U.S.C. 154(b) by 69 days.

(21) Appl. No.: 17/746,798

(22) Filed: May 17, 2022

(65) Prior Publication Data

US 2023/0029805 A1 Feb. 2, 2023

Related U.S. Application Data

(63) Continuation of application No. 17/148,524, filed on Jan. 13, 2021, now Pat. No. 11,331,142.

(30) Foreign Application Priority Data

Jan. 13, 2020 (EP) ..................................... 20382013
Aug. 31, 2020 (EP) ..................................... 20382774

(51) Int. Cl.
*A61B 18/18* (2006.01)
*A61M 25/00* (2006.01)
(Continued)

(52) U.S. Cl.
CPC ......... *A61B 18/18* (2013.01); *A61M 25/0012* (2013.01); *A61M 25/005* (2013.01);
(Continued)

(58) Field of Classification Search
CPC ........ A61N 5/06; A61N 5/0618; A61N 5/062; A61N 5/0622; A61N 2005/0626;
(Continued)

(56) References Cited

U.S. PATENT DOCUMENTS

| | | | |
|---|---|---|---|
| 5,947,977 A | 9/1999 | Slepian et al. | |
| 6,056,745 A | 5/2000 | Panescu et al. | |

(Continued)

FOREIGN PATENT DOCUMENTS

| | | | |
|---|---|---|---|
| CA | 3083870 A1 | 6/2019 | |
| EP | 2120758 A2 | 11/2009 | |

(Continued)

OTHER PUBLICATIONS

Gonzalez-Suarez, et al., "Relation between denaturation time measured by optical coherence reflectometry and thermal lesion depth during radiofrequency cardiac ablation: Feasibility numerical study," Lasers and Surgery in Medicine, 50(3):222-229, Mar. 2018.

(Continued)

*Primary Examiner* — Ahmed M Farah
(74) *Attorney, Agent, or Firm* — Sterne, Kessler, Goldstein & Fox P.L.L.C.

(57) ABSTRACT

Described herein are methods, devices, and support structures for assembling optical fibers in catheter tips and facilitating alignment and structural support. A method for assembling a plurality of optical fibers and lenses in a support structure for an ablation catheter includes providing a support structure with a proximal end, a body, and a distal end, the distal end including a plurality of alignment orifices or slits. A plurality of optical fibers are threaded through the alignment orifices or slits, such that each optical fiber is threaded through a corresponding alignment orifice or slit. An adhesive material is applied at each alignment orifice or slit to secure the optical fibers, and the plurality of optical (Continued)

fibers are then cleaved at the distal end to remove portions of the fibers extending out of the distal end. Finally, a lens is attached to each of the ends of the plurality of optical fibers.

6 Claims, 28 Drawing Sheets

(51) Int. Cl.
    *G02B 6/26*      (2006.01)
    *A61B 17/00*      (2006.01)
    *A61B 18/00*      (2006.01)

(52) U.S. Cl.
    CPC .... *G02B 6/262* (2013.01); *A61B 2017/00292* (2013.01); *A61B 2018/00577* (2013.01); *A61B 2018/1807* (2013.01); *A61M 2025/0096* (2013.01)

(58) Field of Classification Search
    CPC ...... A61N 2005/0627; A61N 2005/063; A61N 2005/0643; A61N 2005/0647; A61N 2005/065; A61N 2005/0658; A61M 2021/0005; A61M 2021/0022; A61M 2021/0027; A61M 2021/0055; A61M 2210/069
    USPC ...................................... 607/88, 89, 101, 109
    See application file for complete search history.

(56) References Cited

U.S. PATENT DOCUMENTS

| | | | |
|---|---|---|---|
| 6,625,351 B2 * | 9/2003 | Cox ....................... | G02B 6/262 385/33 |
| 9,151,913 B2 * | 10/2015 | Selli ........................ | G02B 6/43 |
| 10,413,167 B2 * | 9/2019 | Gmeiner ................ | B33Y 10/00 |
| 10,779,904 B2 | 9/2020 | Ransbury et al. | |
| 11,331,142 B2 | 5/2022 | Sancho Duráet al. | |
| 2001/0031942 A1 | 10/2001 | Tollner et al. | |
| 2002/0031301 A1 * | 3/2002 | Sasaki ...................... | G02B 6/32 385/52 |
| 2003/0208252 A1 | 11/2003 | O'Boyle et al. | |
| 2006/0229515 A1 | 10/2006 | Sharareh et al. | |
| 2007/0270792 A1 | 11/2007 | Hennemann et al. | |
| 2007/0287998 A1 | 12/2007 | Sharareh et al. | |
| 2008/0089641 A1 | 4/2008 | Feldchtein | |
| 2009/0018393 A1 | 1/2009 | Dick et al. | |
| 2009/0306520 A1 | 12/2009 | Schnitt et al. | |
| 2010/0041986 A1 | 2/2010 | Nguyen et al. | |
| 2010/0046953 A1 | 2/2010 | Shaw et al. | |
| 2011/0028967 A1 | 2/2011 | Rollins et al. | |
| 2011/0144524 A1 | 6/2011 | Fish et al. | |
| 2012/0265184 A1 | 10/2012 | Sliwa et al. | |
| 2013/0114924 A1 * | 5/2013 | Loh .......................... | G02B 6/12 385/33 |
| 2014/0052126 A1 | 2/2014 | Long et al. | |
| 2014/0171936 A1 | 6/2014 | Govari et al. | |
| 2015/0209105 A1 | 6/2015 | Margallo Balbas et al. | |
| 2015/0359593 A1 | 12/2015 | Fiser et al. | |
| 2017/0027639 A1 * | 2/2017 | Margallo Balbás . | A61B 5/6852 |
| 2017/0202619 A1 | 7/2017 | Lim | |
| 2018/0168729 A1 | 6/2018 | Pratten et al. | |
| 2018/0214202 A1 | 8/2018 | Howard et al. | |
| 2019/0192005 A1 * | 6/2019 | Duperron ............... | G02B 6/126 |
| 2021/0045834 A1 | 2/2021 | Ransbury et al. | |
| 2022/0280235 A1 * | 9/2022 | Gómez .................. | A61B 18/24 |

FOREIGN PATENT DOCUMENTS

| | | |
|---|---|---|
| EP | 2208475 A1 | 7/2010 |
| EP | 2736434 A1 | 6/2014 |
| EP | 3141181 A1 | 3/2017 |

OTHER PUBLICATIONS

Herranz, D., et al., "Novel catheter enabling simultaneous radiofrequency ablation and optical coherence reflectometry," Biomedical Optics Express, 6(9):3268-75, Aug. 2015.

Herranz, D., et al., "Percutaneous RF Ablation Guided by Polarization-sensitive Optical Coherence Reflectometry in an Integrated Catheter: Experimental Evaluation of the Procedure," Journal of Innovaations in Cardiac Rhythm Management, 6(8):2086-91, Aug. 2015.

Wittkampf, F., et al., "Electroporation and its Relevance for Cardiac Catheter Ablation," JACC: Clinical Electophysiology, 4(8):977-986, Aug. 2018.

International Search Report and Written Opinion of the International Searching Authority directed to related International Patent Application No. PCT/EP2021/050602, dated Apr. 6, 2021; 20 pages.

International Search Report and Written Opinion of the International Searching Authority directed to related International Patent Application No. PCT/EP2021/050603, dated Apr. 12, 2021; 13 pages.

International Search Report and Written Opinion of the International Searching Authority directed to related International Patent Application No. PCT/EP2021/050604, dated Apr. 30, 2021; 11 pages.

Bouchard, Richard, et al. "Photoacoustic characterization of radiofrequency ablation lesions." Photons Plus Ultrasound: Imaging and Sensing 2012. vol. 8223. International Society for Optics and Photonics, 2012. 10 pages.

Iskander-Rizk, Sophinese, et al. "Real-time photoacoustic assessment of radiofrequency ablation lesion formation in the left atrium." Photoacoustics 16 (2019): 100150. 10 pages.

Fleming, Christine, et al., "Optical Coherence Tomography Imaging of Cardiac Radiofrequency Ablation Lesions," Poster presented at Biomedical Optics 2008, St. Petersburg, Florida, Mar. 16-19, 2008; 7 pages.

Fleming, Christine, et al., "Real-Time Imaging of Radiofrequency Cardiac Ablation Using Optical Coherence Tomography," OSA Technical Digest (CD) (Optical Society of America, Mar. 2008), paper BMD88, Mar. 2008; 3 pages.

Boppart, Stephen A., et al., "Real-Time Optical Coherence Tomography for Minimally Invasive Imaging of Prostrate Ablation," Computer Aided Surgery 6:94-103, Accepted Feb. 2001, published online Jan. 2010; 10 pages.

Patel, Nirlep A., et al., "Guidance of Aortic Ablation Using Optical Coherence Tomography," The International Journal of Cardiovascular Imaging 19:171-178, Apr. 2003; 8 pages.

De Boer, Johannes F., et al., "Two-Dimensional Birefringence Imaging in Biological Tissue Using Polarization Sensitive Optical Coherence Tomography," SPIE vol. 3196, 0277, pp. 32-37, Jan. 1998; 6 pages.

"Everett, M.J., et al., ""Birefringence Characterization of Biological Tissue By Use of Opticalcoherence Tomography,"" Optics Letters, vol. 23, No. 3, Feb. 1, 1998; 3 pages."

Fleming, Christine, "Characterization of Cardiac Tissue Using Optical Coherence Tomography," Department of Biomedical Engineering, Case Western Reserve University, May 2010; 210 pages.

\* cited by examiner

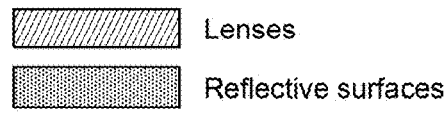 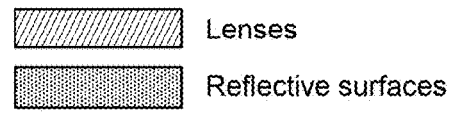
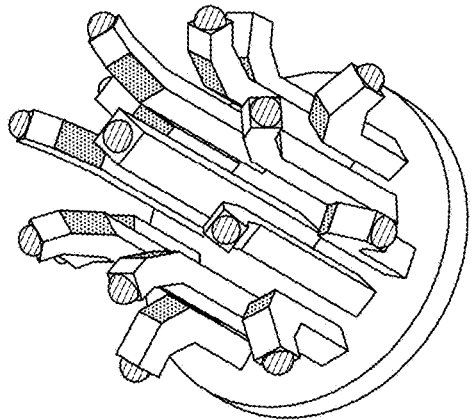 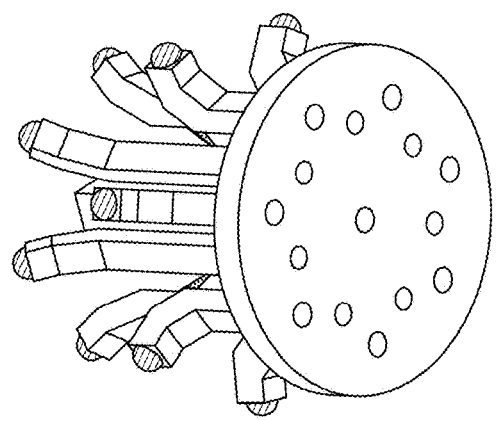
FIG. 31          FIG. 32
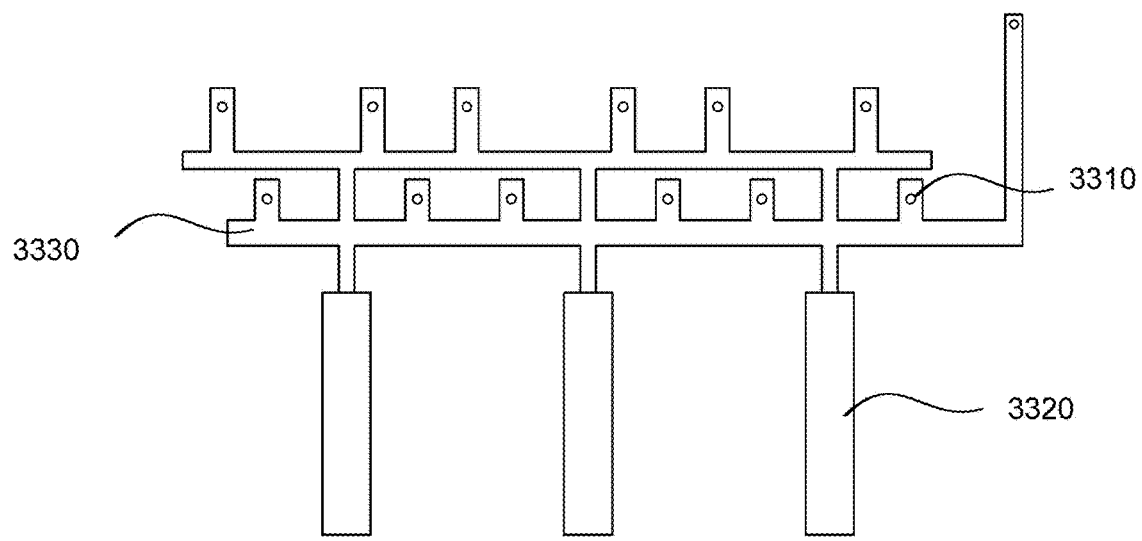
FIG. 33

METHODS, DEVICES, AND SUPPORT STRUCTURES FOR ASSEMBLING OPTICAL FIBERS IN CATHETER TIPS

CROSS-REFERENCE TO RELATED APPLICATIONS

This application is a continuation application of U.S. patent application Ser. No. 17/148,524, filed on Jan. 13, 2021, which claims priority to EP App. No. 20382013.9 filed on Jan. 13, 2020 and EP App. No. 20382774.6 filed on Aug. 31, 2020, the disclosures of which are incorporated by reference herein in their entireties.

BACKGROUND

Field

The present disclosure relates to methods, devices, and support structures for assembling optical fibers in catheter tips and facilitating alignment and structural support.

Background

Ablation is a medical technique for producing tissue necrosis. It is used to help treat different pathologies including cancer, Barret's esophagus, or cardiac arrhythmias, among others. For radiofrequency (RF) ablation, the application of alternating current with an oscillating frequency above several hundreds of kHz avoids the stimulation of excitable tissue while delivering heat by means of the Joule's effect. The increase in tissue temperature produces denaturation of the biological molecules, including proteins such as collagen, myosin, or elastin. Traditionally, RF ablation is done by placing an external electrode on the patient's body, and applying an alternating potential to the tip of a catheter that is placed in contact with the tissue to be treated within the patient's body.

In some cases, various energy sources may be utilized for ablation, including cryogenic cooling for cryoablation, radiofrequency, microwave, laser, ultrasound, and the like. In some cases, cryoablation may use extremely cold temperatures for ablating tissue, whereas electroporation ablation may use pulsed electric fields to ablate specific tissue for the treatment of atrial fibrillation.

The ablation effect depends on a number of factors, including applied electrical power, quality of the electrical contact, local tissue properties, presence of blood flow close to the tissue surface, and the effect of irrigation. Because of the variability of these parameters, it may be difficult to obtain consistent results.

Additionally, ablation catheters using optical fibers may provide variable or inconsistent results if optical fibers are not properly and accurately aligned in catheter tips.

BRIEF SUMMARY

Accordingly, there may be a need for providing new methods, devices, and structures for properly aligning optical fibers in catheter tips in order to obtain accurate results.

In the embodiments presented herein, catheters, support structures, and methods are described for assembling and aligning optical fibers in place at catheter tips for use in tissue ablation procedures. In some embodiments, the optical fibers and lenses in the support structure may be affixed in the catheter tip using various methods and devices, as described herein.

In an embodiment, an example method for assembling a plurality of optical fibers and lenses in a support structure for an ablation catheter is described. The method includes providing a support structure comprising a proximal end, a body, and a distal end, in which the distal end includes a plurality of alignment orifices and threading a plurality of optical fibers through the plurality of alignment orifices at the distal end, in which each optical fiber in the plurality of optical fibers is threaded through a corresponding alignment orifice in the plurality of alignment orifices. The method further includes applying an adhesive material to the plurality of optical fibers and to the distal end, such that the optical fibers are fixed in place in the support structure, cleaving the plurality of optical fibers at the distal end to remove portions of the optical fibers extending out of the distal end of the support structure, and attaching a lens to each of the ends of the plurality of optical fibers, resulting in a plurality of lenses attached to the ends of the optical fibers in the alignment orifices in the distal end. In some embodiments, the alignment orifices may comprise orifices and/or slits.

In another embodiment, a catheter including a proximal section, a distal section, a shaft coupled between the proximal section and the distal section, and a plurality of optical fibers extending through the shaft and to the distal section of the catheter is described. The distal section of the catheter includes a support structure comprising a proximal end, a body, and a distal end. The distal end includes a plurality of alignment orifice and a plurality of lenses, in which each optical fiber in the plurality of optical fibers is threaded through a corresponding alignment orifice in the plurality of alignment orifices, each lens is coupled to an end of a corresponding optical fiber in the plurality of optical fibers and located at the corresponding alignment orifice. A cap is positioned over a portion of the distal end of the support structure. The cap includes a plurality of optical ports, in which locations of the plurality of optical ports are aligned with locations of the plurality of lenses in the plurality of alignment orifices. The support structure is configured to hold the plurality of optical fibers in place and align each optical fiber with the corresponding alignment orifices/slit in the plurality of alignment orifices.

In another embodiment, a support structure for an ablation catheter is described. The support structure includes a proximal end, a body, and a distal end comprising a plurality of alignment orifices. Each optical fiber in a plurality of optical fibers is threaded through a corresponding alignment orifice in the plurality of alignment orifices. Each lens in a plurality of lenses is coupled to an end of a corresponding optical fiber in the plurality of optical fibers, resulting in a plurality of lenses, each lens being located at the corresponding alignment orifice. A cap is positioned over a portion of the distal end of the support structure, in which the cap includes a plurality of optical ports. Locations of the plurality of optical ports are aligned with locations of the plurality of lenses in the plurality of alignment orifices. The support structure is configured to hold the plurality of optical fibers in place and align each optical fiber with the corresponding alignment orifice in the plurality of alignment orifices.

Further features and advantages, as well as the structure and operation of various embodiments, are described in detail below with reference to the accompanying drawings. It is noted that the specific embodiments described herein are not intended to be limiting. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form a part of the specification, illustrate embodiments of the present disclosure and, together with the description, further serve to explain the principles of the disclosure and to enable a person skilled in the pertinent art to make and use the disclosure.

Figure 15:
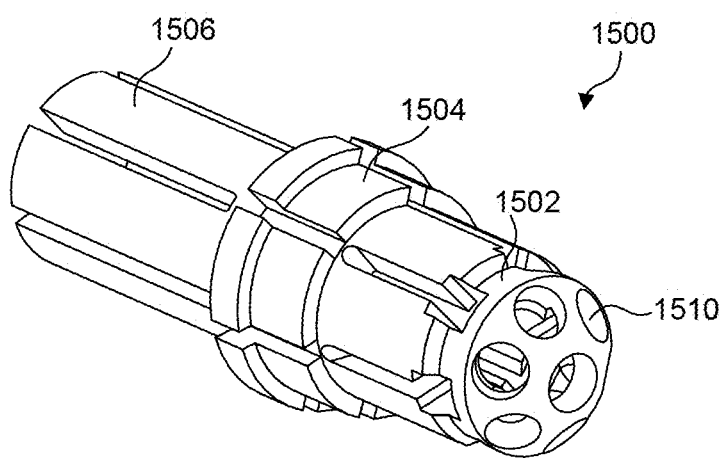

FIG. 15 also illustrates a diagram of an example support structure, according to embodiments of the present disclosure.

Figure 16:
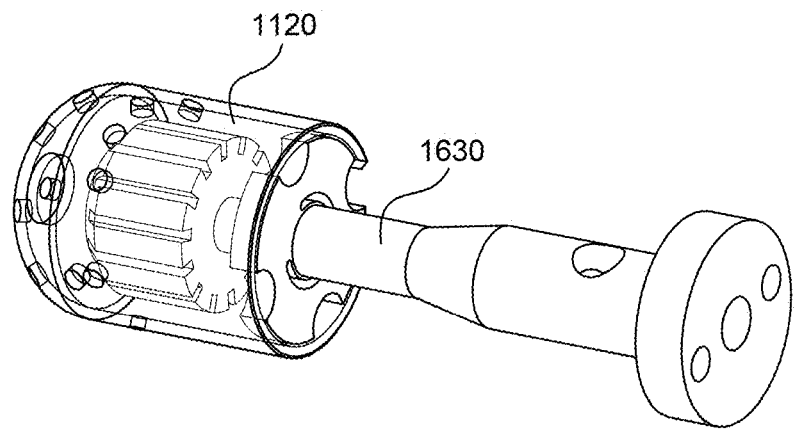

FIG. 16 illustrates a diagram of an example two-part support structure with an inner support structure being used to direct fibers, according to embodiments of the present disclosure.

Figure 17:
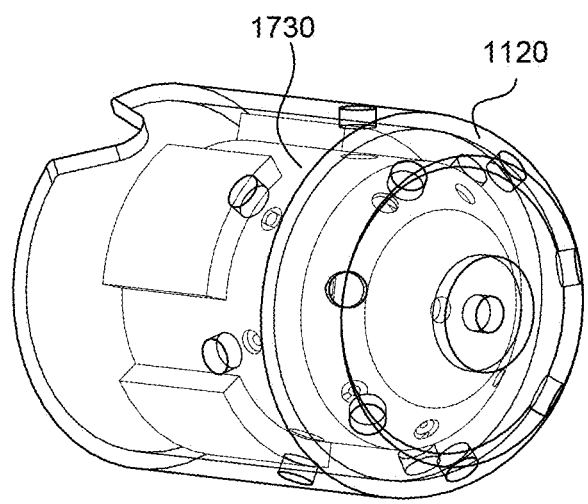

FIG. 17 illustrates a diagram of another example of a two-part support structure with an outer support structure being used to direct fibers, according to embodiments of the present disclosure.

Figure 18:
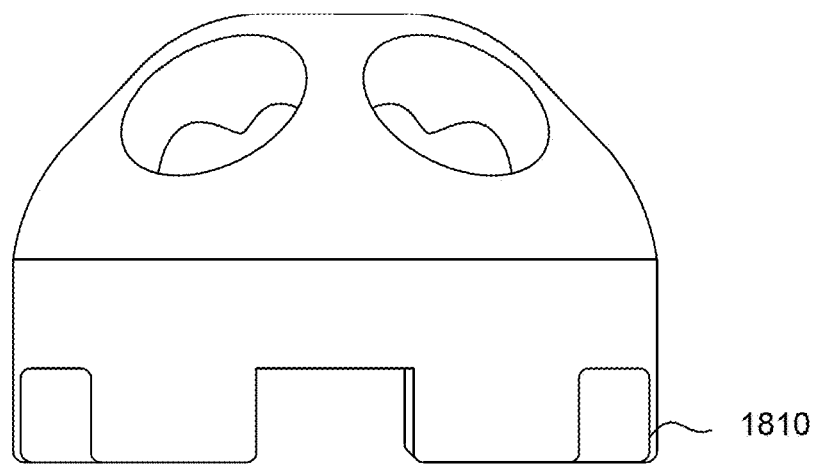

FIG. 18 illustrates a diagram of an example distal end of the support structure, according to embodiments of the present disclosure.

Figure 19:
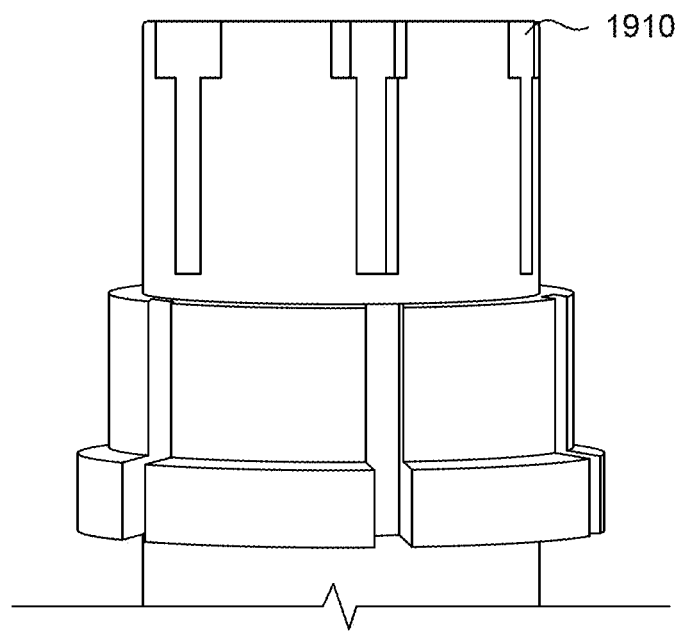

FIG. 19 illustrates a diagram of an example proximal end of the support structure, according to embodiments of the present disclosure.

Figure 20:
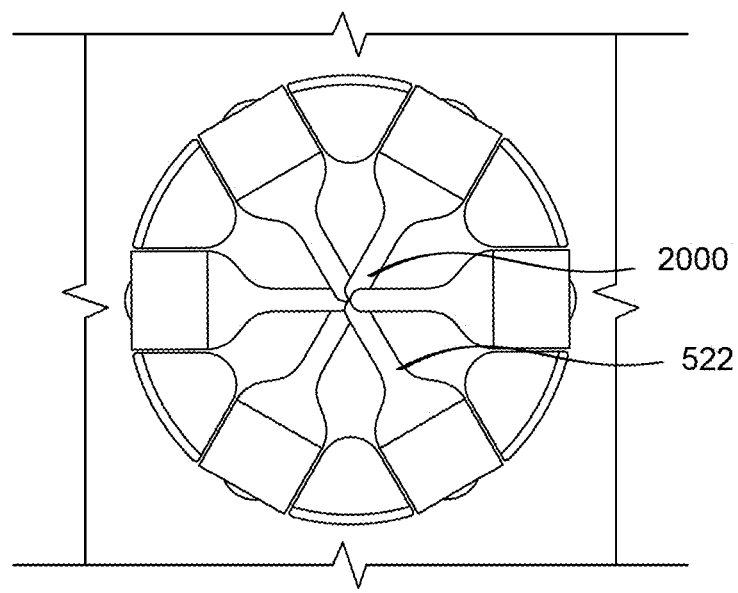

FIG. 20 illustrates a diagram showing an example top view of the body of the support structure, according to embodiments of the present disclosure.

Figure 21:
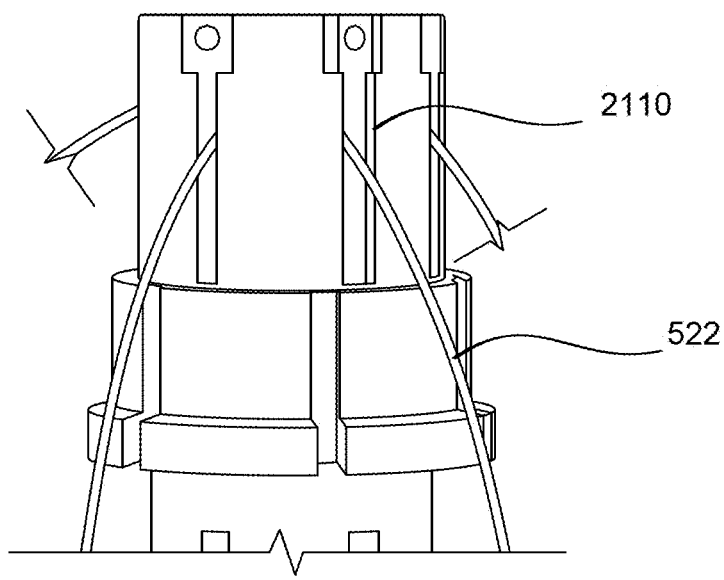

FIG. 21 illustrates a diagram showing an example orientation of optical fibers in the body and the proximal end of the support structure, according to embodiments of the present disclosure.

Figure 22:
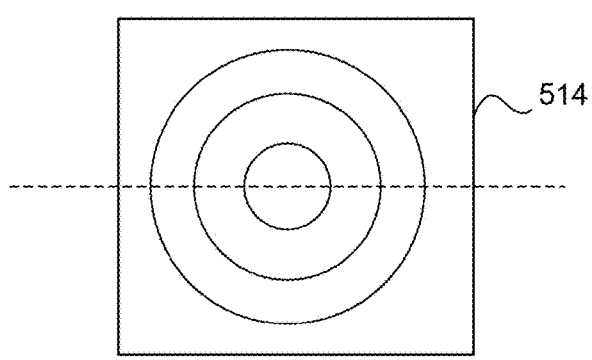

FIG. 22 illustrates a diagram showing an example cross-sectional view of a wafer-based design for a lens arrangement, according to embodiments of the present disclosure.

Figure 23:
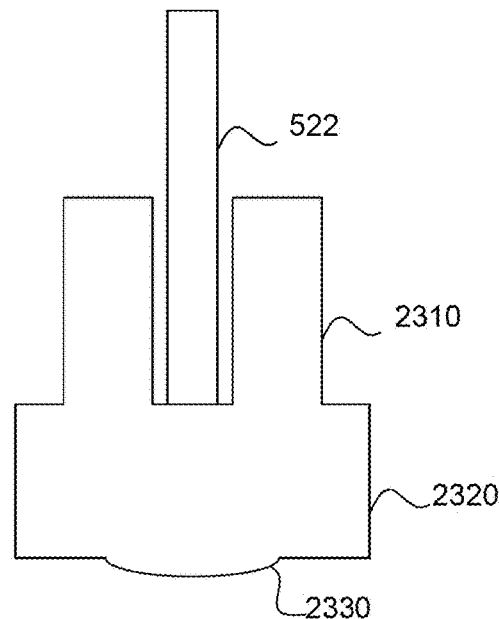

FIG. 23 illustrates a diagram showing an example cross-sectional orthogonal view of a wafer-based design for a lens and optical fiber arrangement, according to embodiments of the present disclosure.

Figure 24:
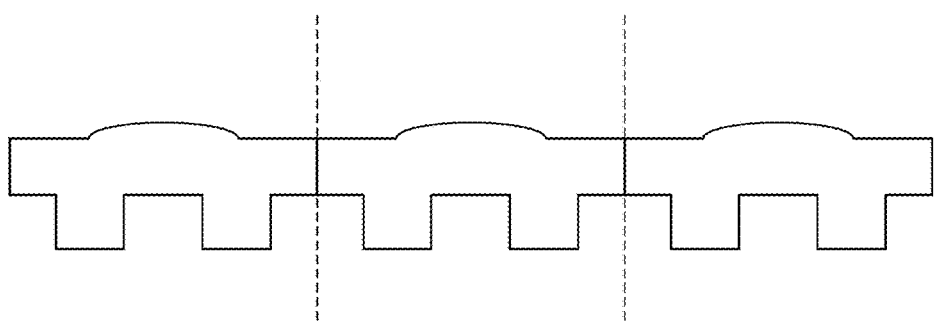

FIG. 24 illustrates a diagram showing an example cross-sectional orthogonal view of a wafer-level assembly of lenses, according to embodiments of the present disclosure.

Figure 25:
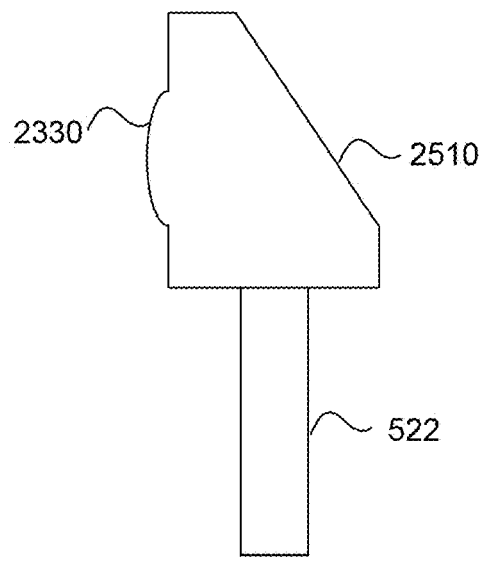

FIG. 25 illustrates a diagram showing an example cross-sectional view of a wafer-based design with a mirror or reflective surface to redirect beams of light, according to embodiments of the present disclosure.

Figure 26:
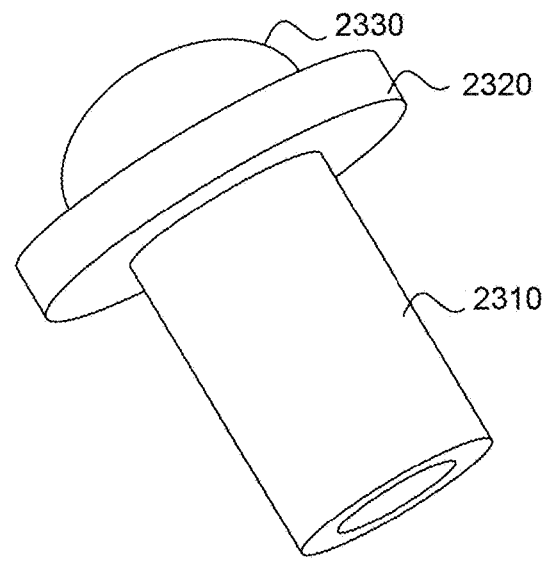

FIG. 26 illustrate a diagram of an example mirror or reflective surfaces added on lenses in different regions for a wafer-based design, according to embodiments of the present disclosure.

Figure 27:
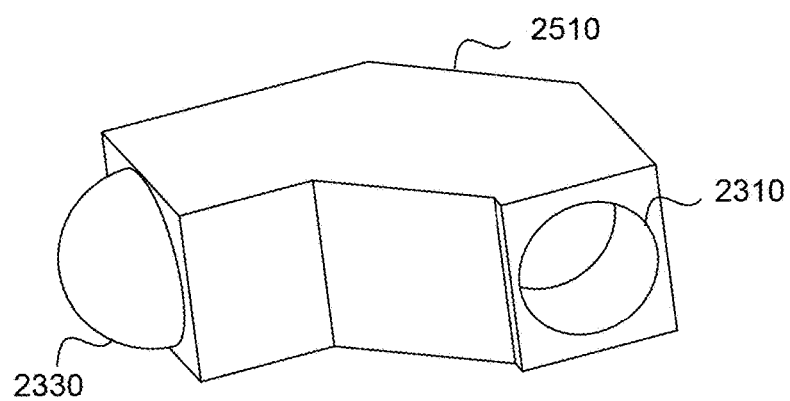
Figure 28A:
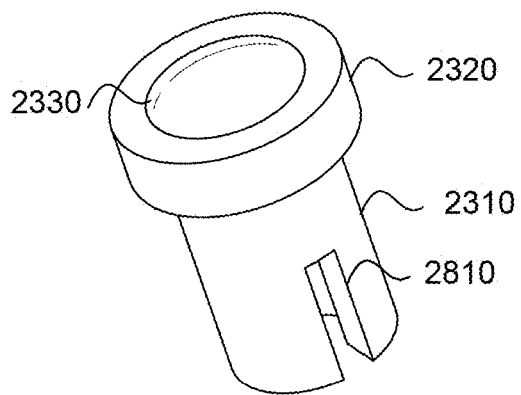
Figure 28B:
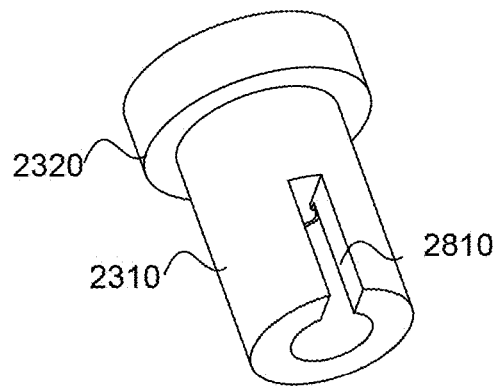
Figure 28C:
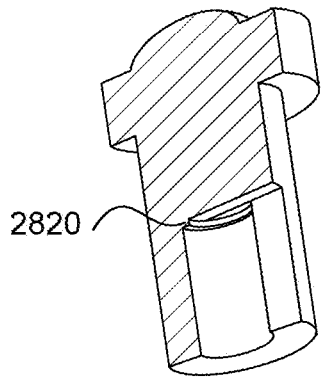
Figure 28D:
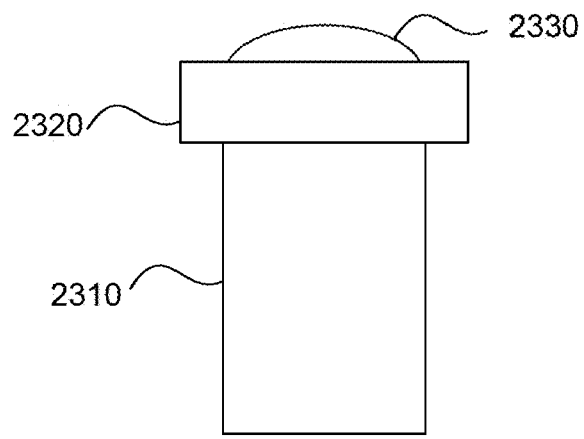

FIG. 27 illustrate a diagram of an example mirror or reflective surfaces added in different regions for a wafer-based design, according to embodiments of the present disclosure.

FIGS. 28A-D illustrate diagrams of an example lens structures for attaching to fiber ends, according to embodiments of the present disclosure.

Figure 29:
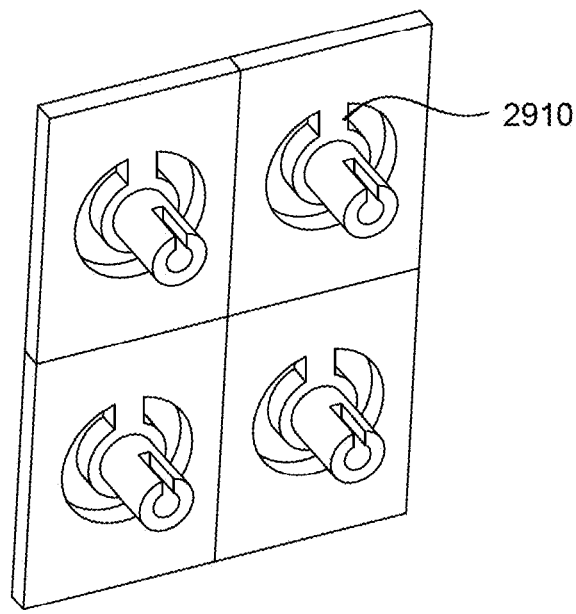

FIG. 29 illustrates a diagram n example showing a view of additional lens structures in a wafer design, according to embodiments of the present disclosure.

Figure 30:
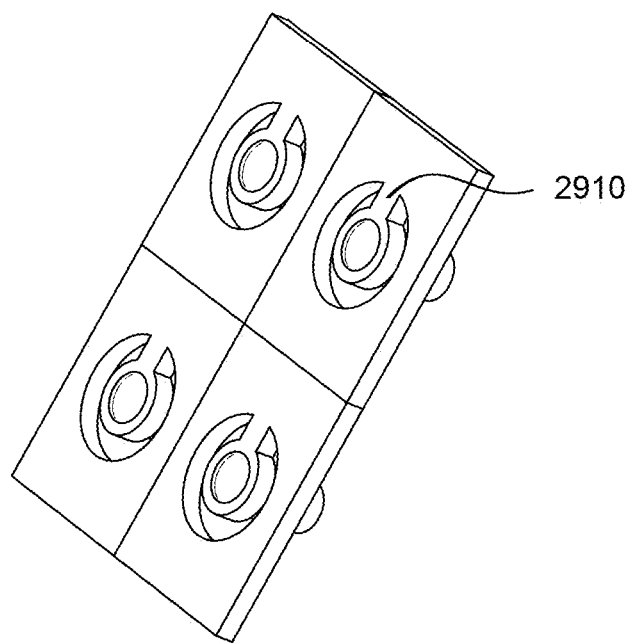

FIG. 30 illustrates a diagram showing another example view of additional lens structures in a wafer design, according to embodiments of the present disclosure.

FIG. 31 illustrates a diagram showing an example arrangement of the plurality of fibers with lenses and reflective surfaces, according to embodiments of the present disclosure.

FIG. 32 illustrates a diagram showing example orifices for the fiber optics in the arrangement of the plurality of fibers with lenses and reflective surfaces, according to embodiments of the present disclosure.

FIG. 33 illustrates a block diagram of an example multiple multiplexing light transmission structure, according to embodiments of the present disclosure.

Figure 34:
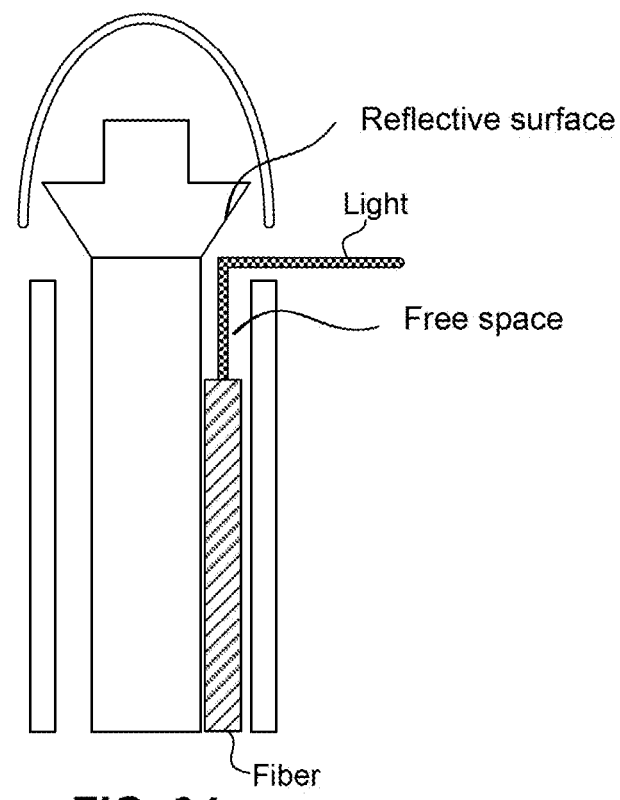

FIG. 34 illustrates a diagram of an example design in which light beams are directed to prevent bending of fibers or waveguides, according to embodiments of the present disclosure.

Figure 35:
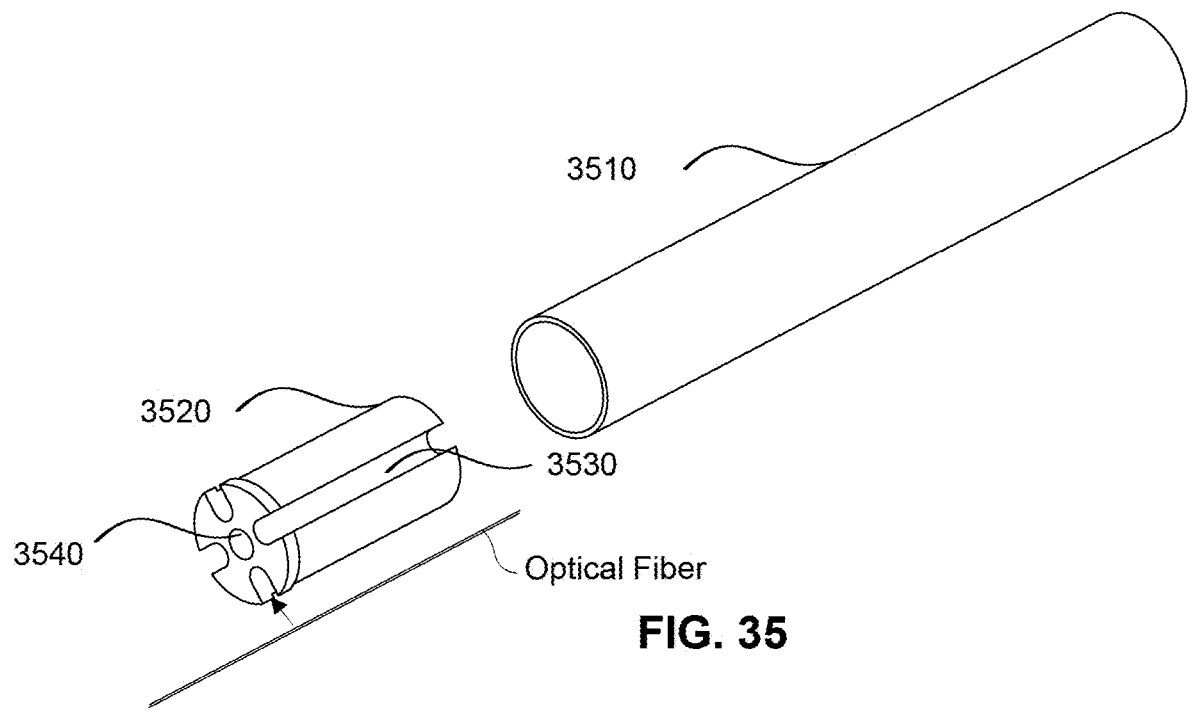

FIG. 35 illustrates a diagram of an example shaft of a catheter constructed from and inserted with slits and/or orifices and an external sheath.

Figure 36A:
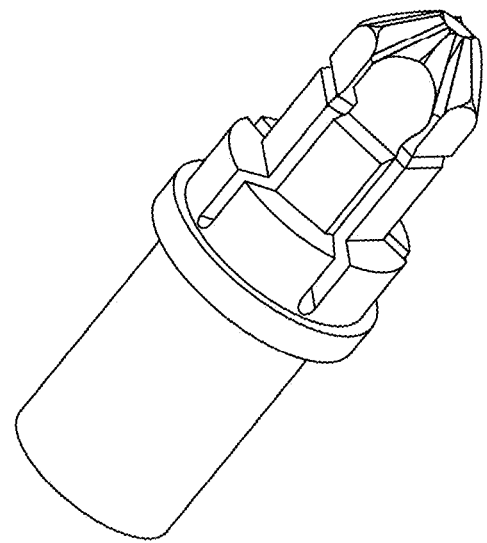

FIG. 36A illustrates a diagram of a n example support structure design for the catheter tip, according to embodiments of the present disclosure.

Figure 36B:
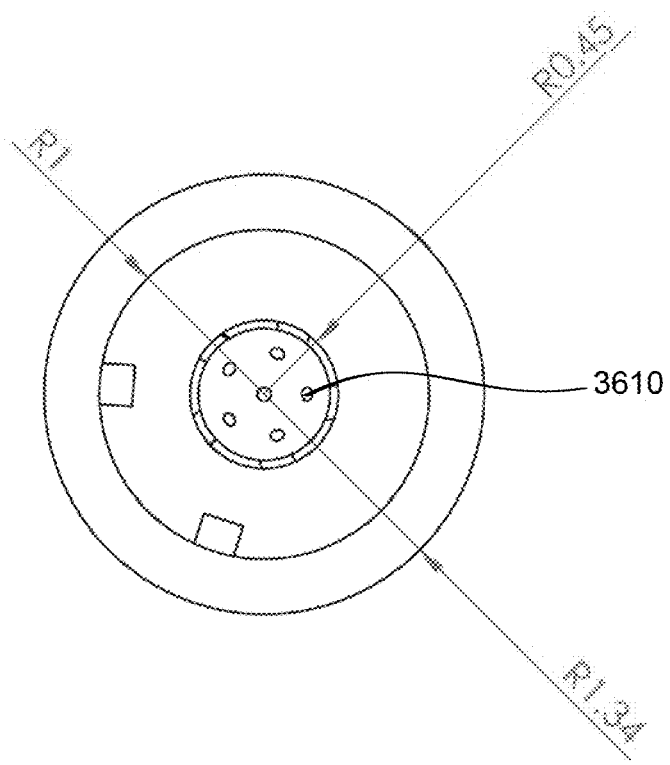

FIG. 36B illustrates a diagram of an example cross-section of the distal end of the support structure design shown in FIG. 36A, according to embodiments of the present disclosure.

Figure 36C:
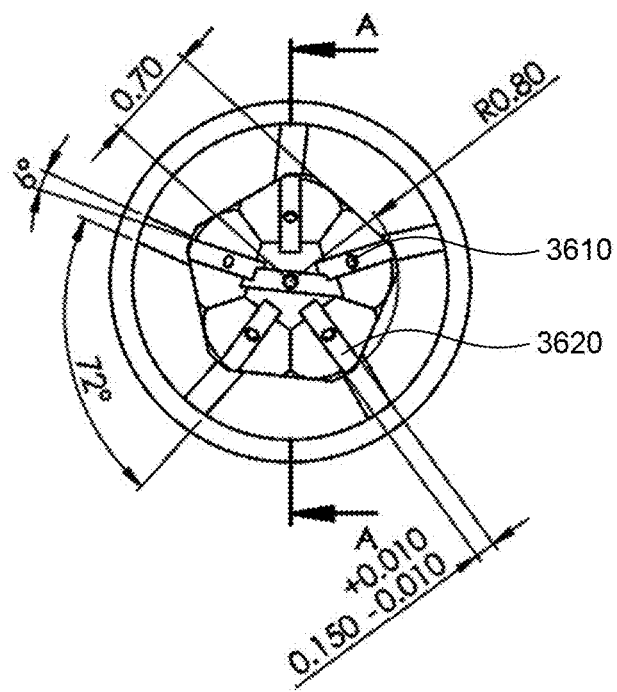

FIG. 36C illustrates a diagram of an example top view of the distal end of the support structure design shown in FIG. 36A, according to embodiments of the present disclosure.

Figure 36D:
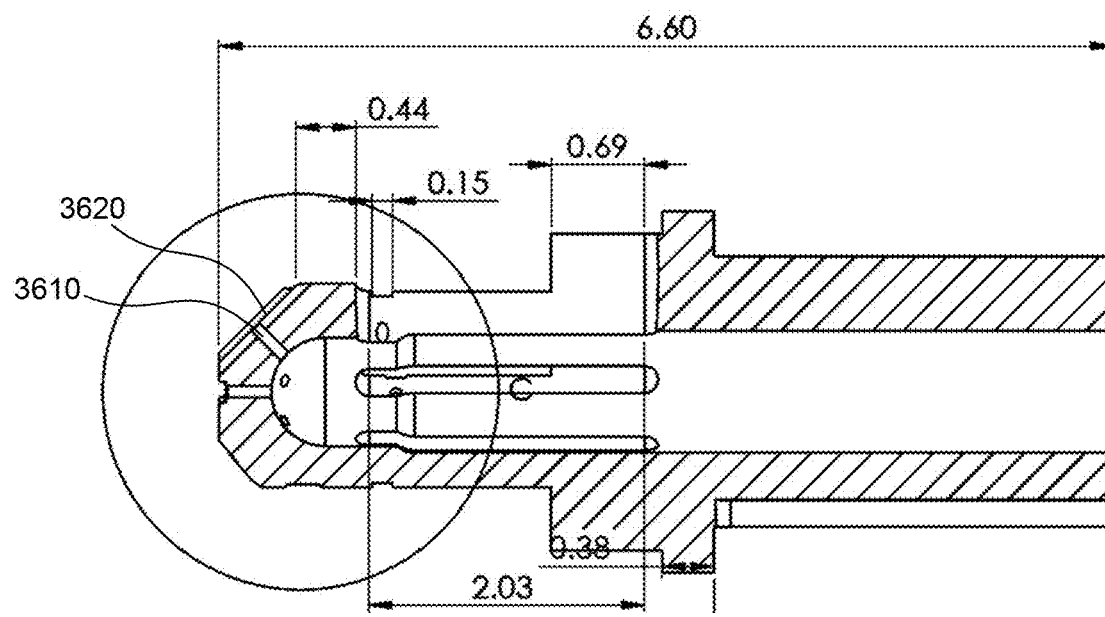

FIG. 36D illustrates a diagram of an example cross-section of a side view of the support structure design shown in FIG. 36A, according to embodiments of the present disclosure.

Figure 37A:
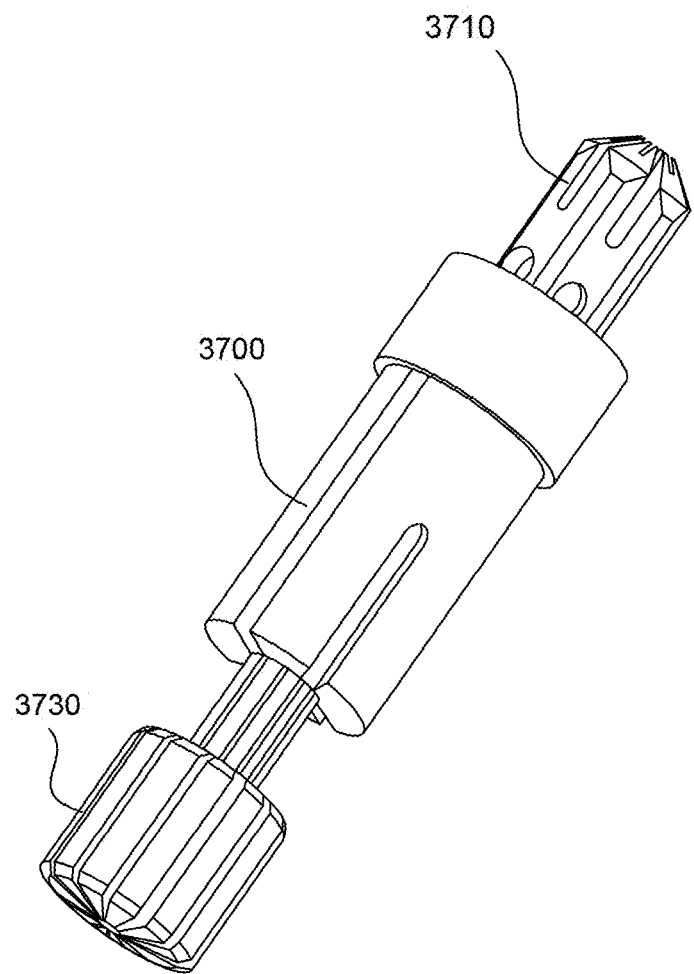

FIG. 37A illustrates a diagram of an example fiber alignment tool arranged in a distal end of a support structure, according to embodiments of the present disclosure.

Figure 37B:
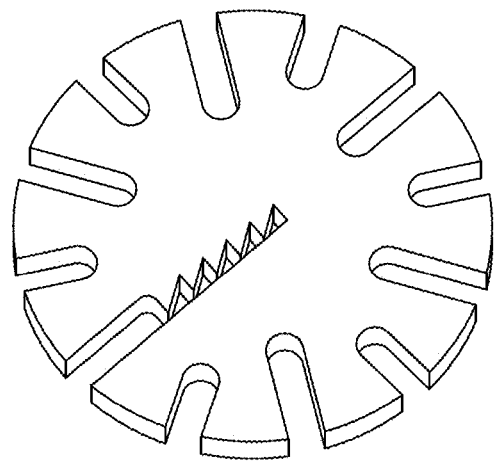

FIG. 37B illustrates a diagram of an example of a cross-sectional view of slit patterns that may be used as part of the fiber alignment tool assembly process, according to embodiments of the present disclosure.

Figure 37C:
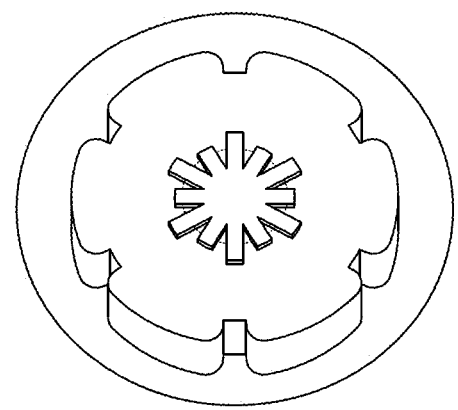

FIG. 37C illustrates a diagram of an example of a cross-sectional view of slit patterns that may be used as part of the fiber alignment tool assembly process, according to embodiments of the present disclosure.

Figure 37D:
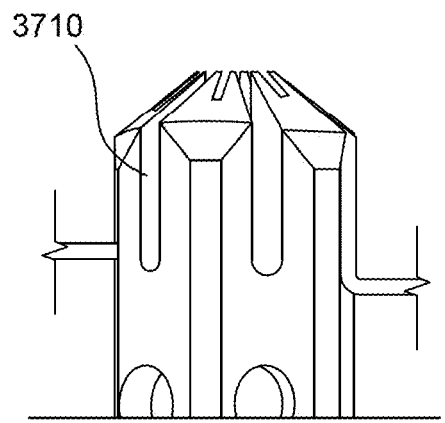

FIG. 37D illustrates a diagram illustrating an example diagram of a distal end of a support structure with fiber alignment slits, according to embodiments of the present disclosure.

Figure 37E:
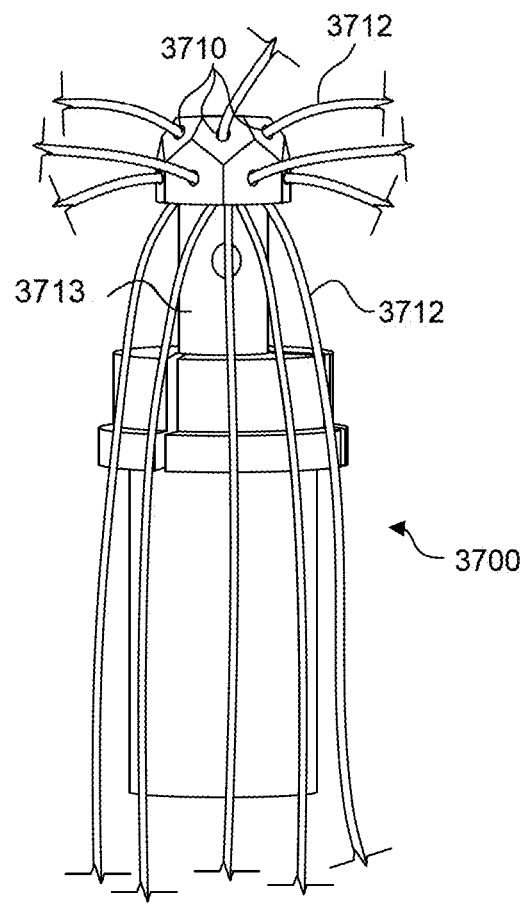

FIG. 37E illustrates an additional example diagram showing an example arrangement of optical fibers in the support structure, according to embodiments of the present disclosure.

Figure 38A:
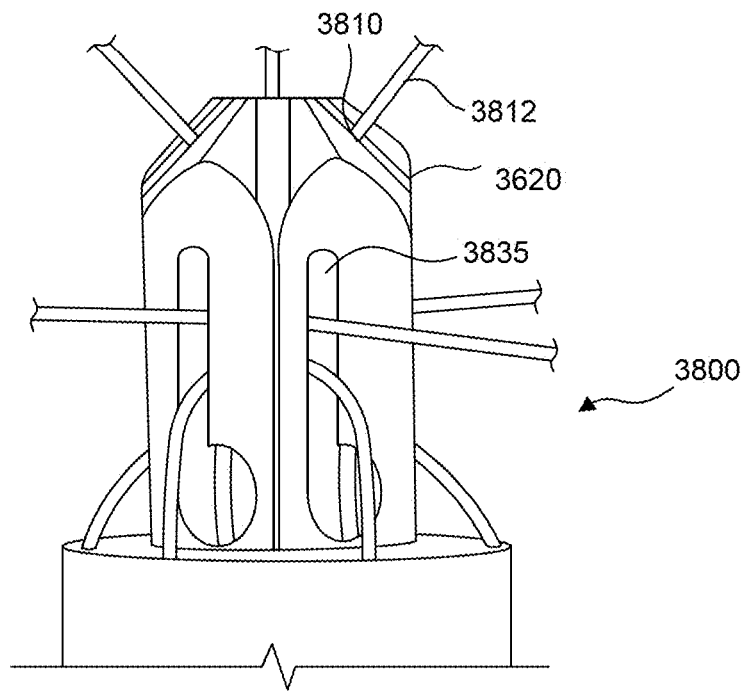

FIG. 38A illustrates a diagram showing an example arrangement of optical fibers in the support structure, according to embodiments of the present disclosure.

Figure 38B:
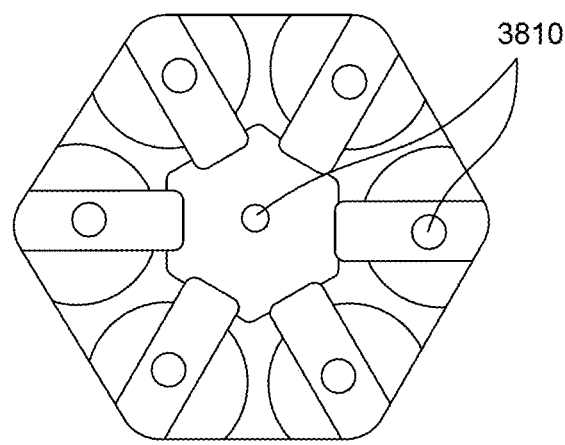

FIG. 38B illustrates a diagram of an example top view of the distal end of the support structure, according to embodiments of the present disclosure.

Figure 38C:
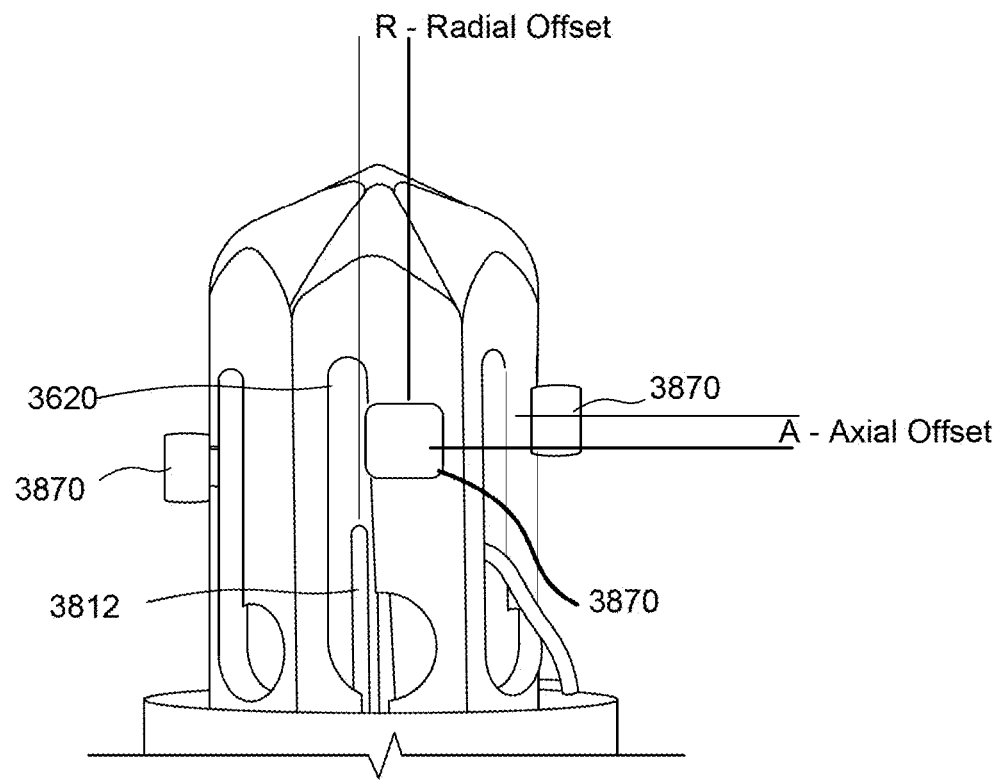

FIG. 38C illustrates a diagram of an example side view of the distal end of the support structure after arrangement, cleaving, gluing, and polishing of the fibers within support structure, according to embodiments of the present disclosure.

Figure 38D:
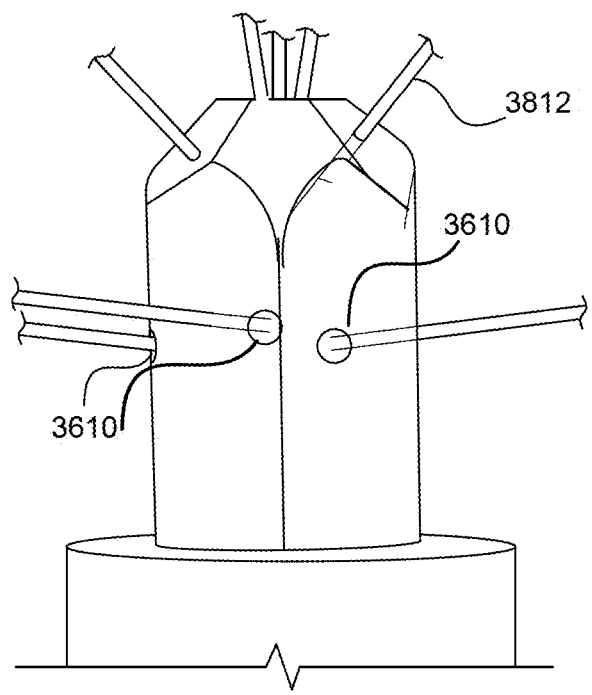

FIG. 38D illustrates a diagram of an example support structure, according to embodiments of the present disclosure.

Figure 38E:
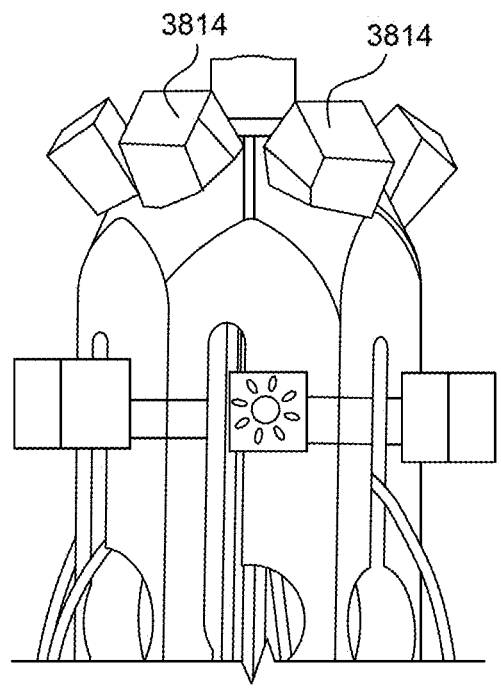

FIG. 38E illustrates a diagram of an example support structure with lenses attached, according to embodiments of the present disclosure.

Figure 38F:
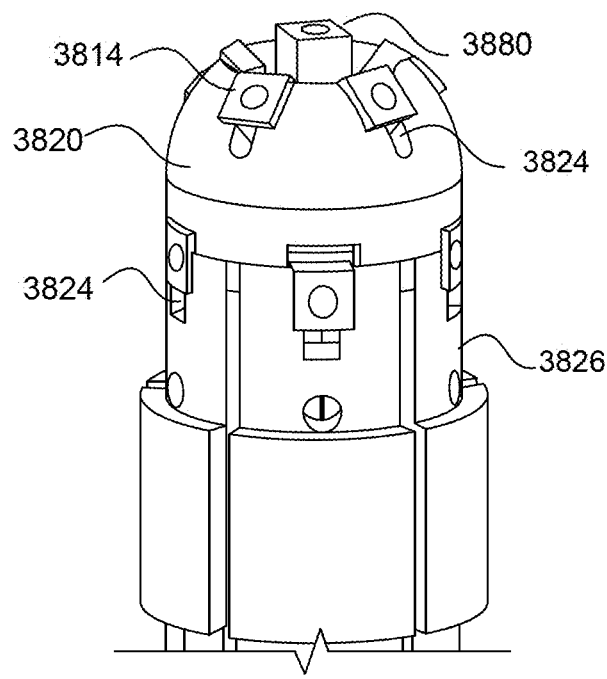

FIG. 38F illustrates a diagram showing an example two-part support structure with lenses attached, according to embodiments of the present disclosure.

Figure 39:
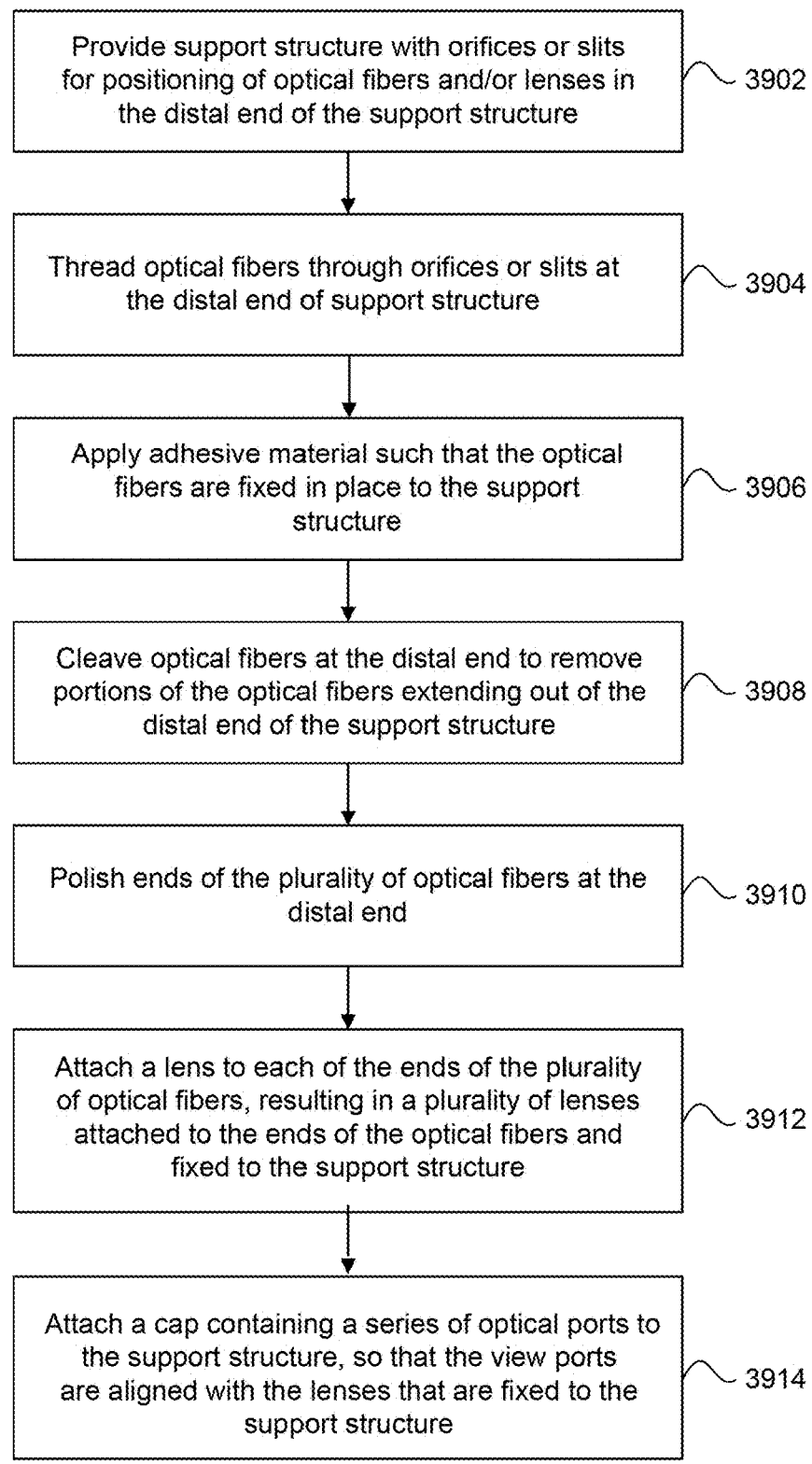

FIG. 39 illustrates an example method for assembling a plurality of optical fibers and lenses in a support structure for an ablation catheter, according to embodiments of the present disclosure.

Figure 40:
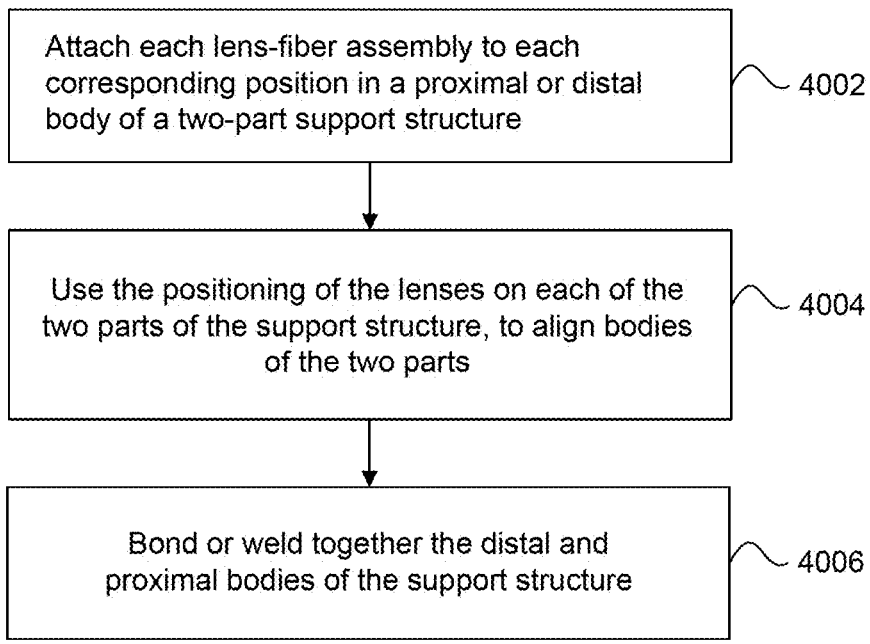

FIG. 40 illustrates another example method for assembling a plurality of optical fibers and lenses in a two-part/body support structure for an ablation catheter, according to embodiments of the present disclosure.

Embodiments of the present disclosure will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present disclosure. It will be apparent to a person skilled in the pertinent art that this disclosure can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

It should be noted that although this application may refer specifically to cardiac ablation, the embodiments described herein may target other pathologies as well, along with additional energy sources for ablation, including but not limited to cryogenic, radiofrequency (RF), microwave, laser, ultrasound, and pulsed electric fields. The principles of using laser energy to treat other pathologies are similar, and therefore the techniques used to apply the laser energy are similar.

Disclosed herein are embodiments of an ablation catheter for merged optical tissue evaluation and laser ablation in which the ablation catheter includes a plurality of optical ports for both evaluating and ablating target tissue. In some embodiments, the plurality of optical ports of the catheter may be configured to transmit beams of exposure radiation to a sample, receive one or more beams of scattered radiation that have been reflected or scattered from the sample, and transmit laser energy such that at least a portion of the sample is ablated. By utilizing the same optical ports for transmission of the optical evaluation signals and the laser ablation signals, the ablation catheter may provide focused evaluation of the same target tissue that is being ablated in a single substrate that allows for both modalities.

Herein, the terms "electromagnetic radiation," "light," and "beam of radiation" are all used to describe the same electromagnetic signals propagating through the various described elements and systems.

Exemplary Catheter Embodiments

Figure 1:
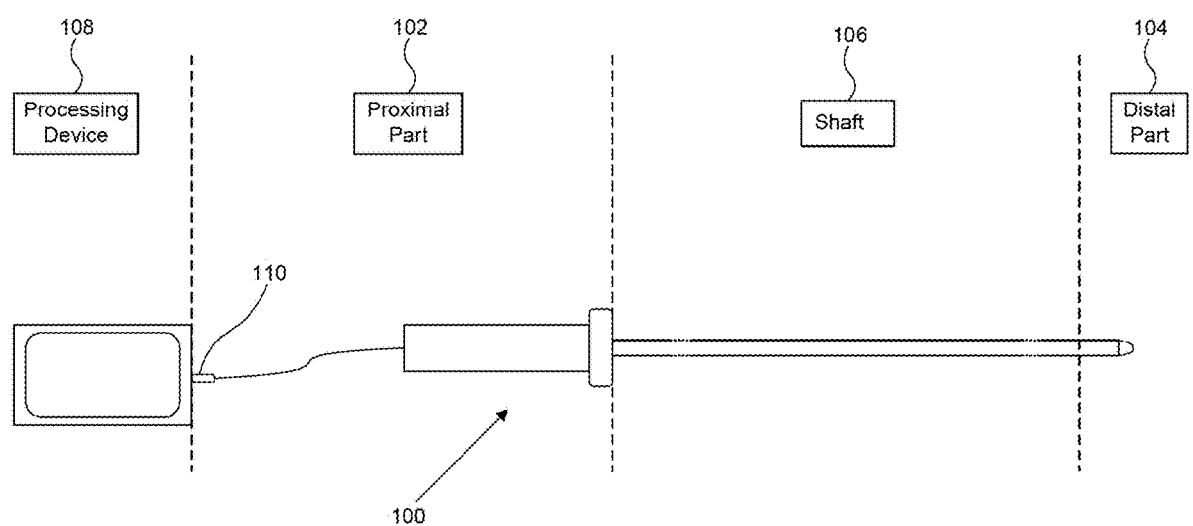
FIG. 1 illustrates an example diagram of a catheter, according to embodiments of the present disclosure.

FIG. 1 illustrates a catheter 100 according to embodiments of the present disclosure. Catheter 100 includes a proximal section 102, a distal section 104, and a shaft 106 coupled between proximal section 102 and distal section 104. In an embodiment, shaft 106 includes one or more radiopaque markers for navigation purposes. In one embodiment, catheter 100 includes a communication interface 110 between catheter 100 and a processing device 108. Communication interface 110 may include one or more one or more optical fibers and connectors between processing device 108 and catheter 100, as described herein. In other examples, communication interface 110 may include an interface component that allows wireless communication, such as Bluetooth, WiFi, cellular, and the like, to communicate with the catheter 100 or other processing components in a catheter system In an embodiment, shaft 106 and distal section 104 are disposable. As such, proximal section 102 may be reused by attaching a new shaft 106 and proximal section 104 each time a new procedure is to be performed. In another embodiment, proximal section 102 is also disposable.

Proximal section 102 may house various electrical and optical components used in the operation of catheter 100. A first optical source may be included within proximal section 102 to generate a source beam of radiation for optical evaluation. The first optical source may include one or more laser diodes or light emitting diodes (LEDs). The beam of radiation generated by the optical source may have a wavelength within the infrared range. In one example, the beam of radiation has a central wavelength of 1.3 µm. The optical source may be designed to output a beam of radiation at only a single wavelength, or it may be a swept source and be designed to output a range of different wavelengths. The generated beam of radiation may be guided towards distal section 104 via the optical transmission medium connected between proximal section 102 and distal section 104 within shaft 106. Some examples of optical transmission media include single mode optical fibers and/or multimode optical fibers. In one embodiment, the electrical transmission medium and the optical transmission medium are provided by the same hybrid medium allowing for both electrical and optical signal propagation.

Furthermore, proximal section 102 may include a second optical source, such as a laser energy source, to generate laser energy that is applied at distal section 104 for tissue ablation. In some embodiments, the laser energy source may emit an ablation beam of laser energy at a wavelength of 980 nm or a wavelength of 1060 nm. The laser energy from the source in the proximal section 102 may propagate down the catheter 100 via an optical transmission medium connected between proximal section 102 and distal section 104 within shaft 106, and the laser energy may be output from the distal section 104 of catheter 100 to target tissue. For example, the laser energy from the source may produce an optical power of 5 W to 12 W that is applied to target tissue for 20-30 seconds to produce transmural lesions in heart tissue. In another example, the laser energy from the source may produce an optical power of 30 W to 50 W that is applied to target tissue for 60-90 seconds.

In an embodiment, proximal section 102 includes one or more components of an interferometer in order to perform low coherence interferometry (LCI) using the light generated from the second optical source. Due to the nature of interferometric data analysis, in an embodiment, the optical transmission medium used for guiding the light to and from distal section 104 does not affect the state and degree of light polarization. In another embodiment, the optical transmission medium affects the polarization in a constant and reversible way. In some embodiments, catheter 100 may include an optical circuit with one or more elements configured to conduct optical spectroscopy. In such embodiments, at least part of the optical path may be made up of multi-mode optical transmission media (e.g. multi-mode optical fiber).

Proximal section 102 may include further interface elements with which a user of catheter 100 can control the operation of catheter 100. For example, proximal section 102 may include a deflection control mechanism that controls a deflection angle of distal section 104. The deflection control mechanism may include a mechanical movement of an element on proximal section 102, or the deflection control mechanism may use electrical connections to control the movement of distal section 104. Proximal section 102 may include various buttons or switches that allow a user to control when laser energy is applied at distal section 104, or when the beams of radiation are transmitted from distal section 104, allowing for the acquisition of optical data. In some embodiments, proximal section 102 may include a deflection control mechanism for controlling one or more pull wires that are coupled to the distal section 104. In some embodiments, deflection control mechanism and the one or more pull wires allow for steering of the distal section of catheter 100 in order to maneuver within and target specific tissue regions for ablation.

Distal section 104 includes a plurality of optical view ports. In some embodiments, the plurality of optical view ports may be referred to herein as orifices in the catheter tip.

In an embodiment, one or more of the optical view ports are machined into the outer body of distal section 104. The optical view ports are distributed over the outside of distal section 104, resulting in a plurality of distinct viewing directions. In some embodiments, the optical view ports may transmit and collect light (e.g., optical signals) at various angles from the distal section 104. The optical view ports also allow for a plurality of directions (e.g., beam directions) in which laser energy may be directed for tissue ablation through one or more of the optical view ports. In an embodiment, each of the plurality of viewing directions are substantially non-coplanar. The optical view ports may also be designed with irrigation functionality to cool distal section 104 and surrounding tissue during ablation.

Figure 2A:
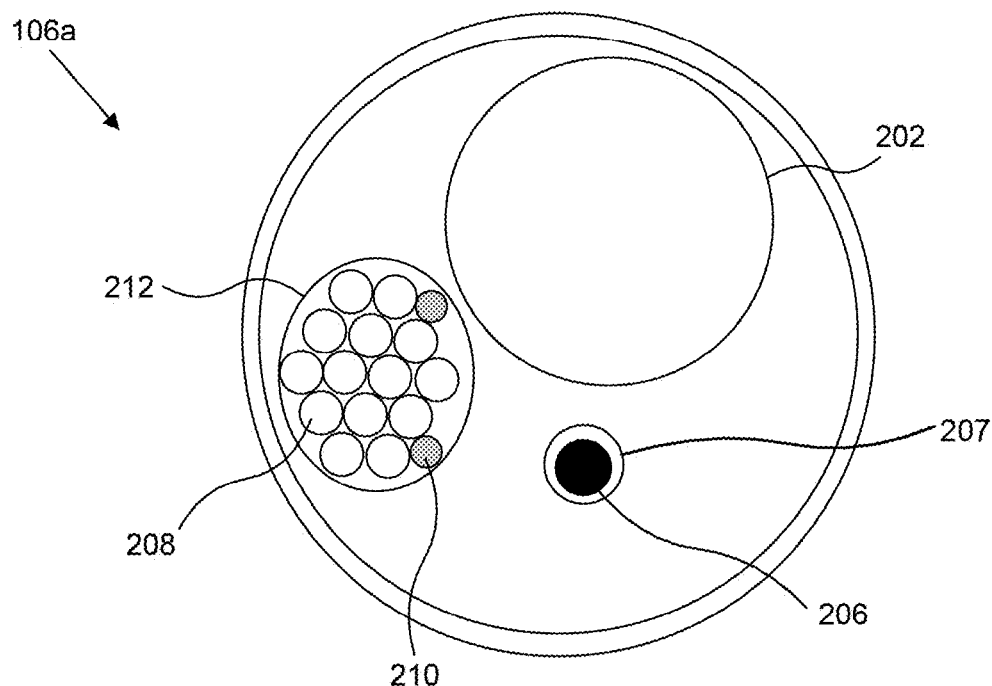
FIGS. 2A and 2B illustrate cross sections of a catheter, according to embodiments of the present disclosure.
Figure 2B:
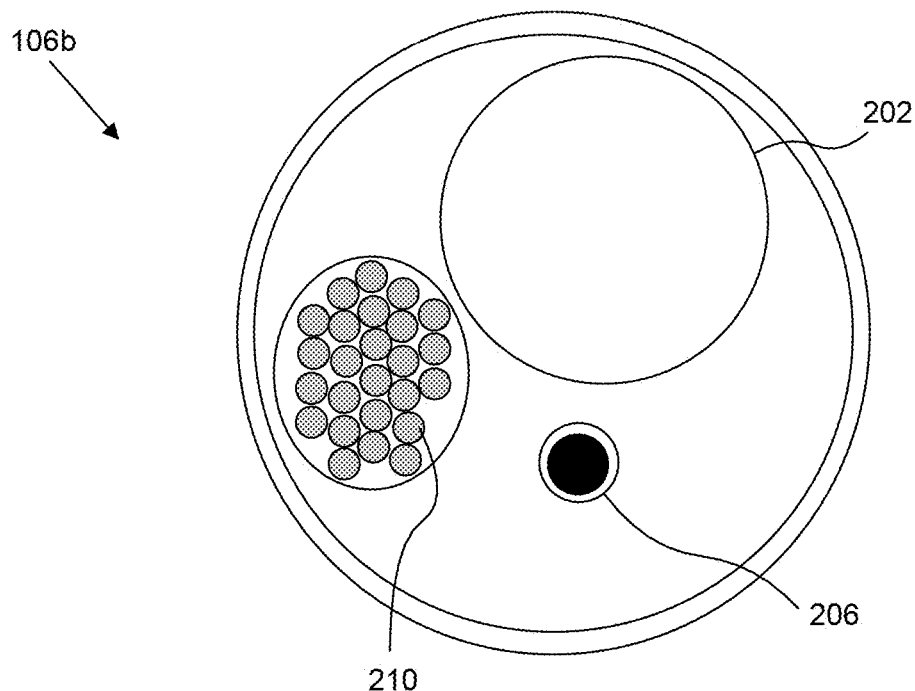

FIGS. 2A and 2B illustrate cross-section views of shaft 106, according to embodiments of the present disclosure. Shaft 106 may include all of the elements interconnecting proximal section 102 with distal section 104. Shaft 106*a* illustrates an embodiment that houses multiple channels/lumens, including an irrigation channel 202, a cabling channel 212, and a channel for deflection mechanisms 207. Through these channels 207, 212, 202, deflection mechanism 206, electrical connections 208, and optical transmission medium 210, and cooling fluid may be at least partially housed or transported. In some configurations, a protective cover wrapped around both electrical connections 208 and optical transmission media 210 may be used. In other embodiments, optical transmission media 210 and components may be located within a protective cover that is separate from the protective cover in which the electrical connections 208 is housed. Electrical connections 208 may be used to provide signals to optical modulating components located in distal section 104. One or more optical transmission media 210 guide light generated from the optical source (exposure light) towards distal section 104, while another subset of optical transmission media 210 guides light returning from distal section 104 (scattered or reflected light) back to proximal section 102. In another example, the same one or more optical transmission media 210 guides light in both directions. In some embodiments, the optical transmission medium 210 comprises one or more single mode optical fibers and/or multimode optical fibers.

Irrigation channel 202 may be a hollow tube used to guide cooling fluid towards distal section 104. Irrigation channel 202 may include heating and/or cooling elements disposed along the channel to affect the temperature of the fluid. In another embodiment, irrigation channel 202 may also be used as an avenue for drawing fluid surrounding distal section 104 back towards proximal section 102.

Deflection mechanism 206 may include electrical or mechanical elements designed to provide a signal to distal section 104 in order to change a deflection angle of distal section 104. The deflection system enables guidance of distal section 104 by actuating a mechanical control placed in proximal section 102, according to an embodiment. This system may be based on a series of aligned and uniformly spaced cutouts in shaft 106 aimed at providing unidirectional deflection of distal section 104, in combination with a wire which connects the deflection mechanism control in proximal section 102 with the catheter tip at distal section 104. In this way, a certain movement of the proximal section may be projected to the distal section. Other embodiments involving the combination of several control wires attached to the catheter tip may enable the deflection of the catheter tip along different directions.

FIG. 2B illustrates a cross-section of shaft 106*b*. Shaft 106*b* depicts an embodiment having most of the same elements as shaft 106a from FIG. 2A, except that there are no electrical connections 208. Shaft 106b may be used in situations where modulation (e.g., multiplexing) of the generated beam of radiation is performed in proximal section 102.

Exemplary Catheter System and Console Embodiments

Figure 3:
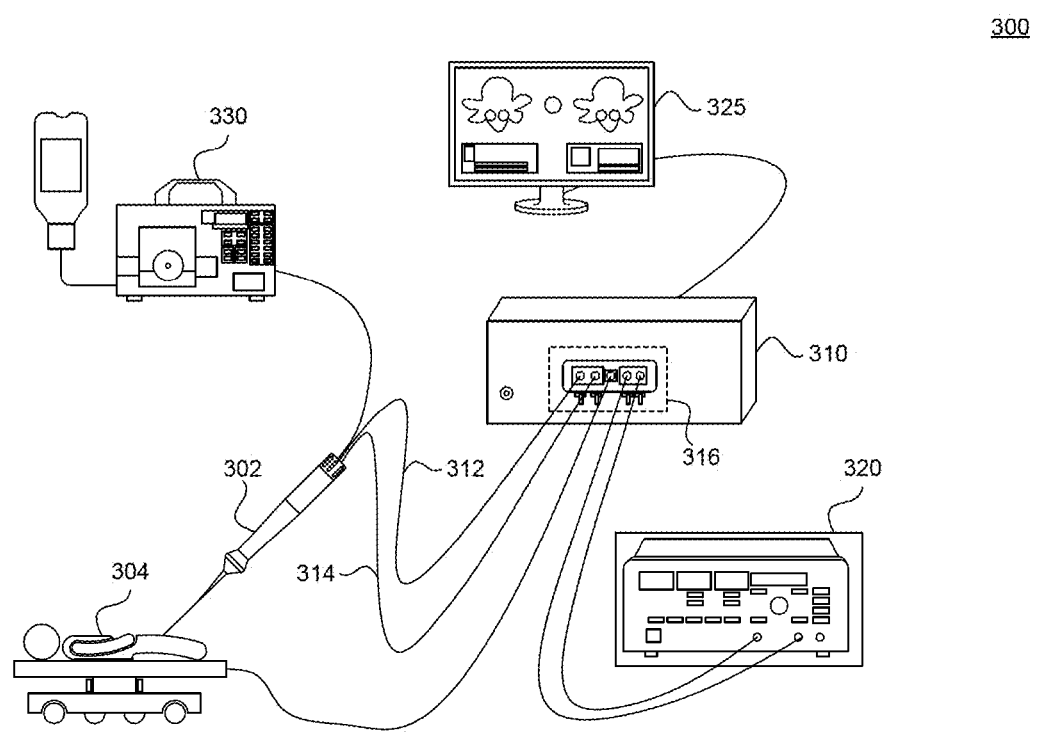
FIG. 3 illustrates a diagram of an example system for ablation, according to embodiments of the present disclosure.

In some embodiments, an ablation catheter and console system described herein uses optical coherence tomography (OCT) and/or optical coherence reflectometry (OCR), refractometry, or other methods to perform tissue ablations, track scar formation in real-time, and monitor/verify lesion geometries and isolation by directly observing the scar pattern in tissue. FIG. 3 illustrates a diagram of an example system 300 for performing ablation according to embodiments of the present disclosure. The system 300 includes catheter 302, console 310, signal generator 320, display 325, and irrigation pump 330. The catheter 302, console 310, signal generator 320, display 325, and irrigation pump 330 may be communicatively coupled together via wired and/or wireless connections. In some embodiments, catheter 302 may represent an exemplary embodiment of catheter 100 shown in FIG. 1. In some embodiments, patient 304 is shown in FIG. 3 for illustrative purposes. It is understood that the embodiments described herein may be used in vivo and/or in vitro.

In some embodiments, catheter 302 may be positioned at a portion of tissue subject to ablation using energy generated by signal generator 320. In some embodiments, signal generator 320 may be an electronic device configured to generate radiofrequency (RF), cryogenic, or electroporation (e.g., pulsed electric field) signals for ablation. The signal generator 320 may be coupled to catheter 302 directly or via the console 310, and may send energy to catheter 302 to ablate the portion of tissue at a selected tissue site. In some embodiments, the portion of tissue may comprise myocardial tissue, cardiac muscle tissue, skeletal tissue, or the like. Energy may be applied to the portion of tissue through optical view ports in the distal section of catheter 302. After applying the energy, structural changes in the tissue may be observed by acquiring optical signals via one or more optical view ports of catheter 302.

Console 310 may comprise a computing device configured to acquire the optical signals from catheter 302 and analyze the optical signals to detect changes in optical properties of the tissue. In some embodiments, console 310 may include hardware (e.g., circuits), firmware, software, or any combination thereof to process the optical signals and perform further analysis. In some embodiments, console 310 may send light through an optical circuit within itself and the catheter 302 and into the tissue to monitor scar progression, contact between the tissue and catheter 302, and other characteristics of the tissue. In some embodiments, console 310 may be referred to herein as a control console, a processing device, and/or controller. Console 310 may be coupled to display 325, which may present results from the optical signal analysis and allow a user to select/view, modify, and/or control parameters related to operation of catheter 302, console 310, signal generator 320, and/or irrigation pump 330.

In some embodiments, irrigation pump 330 may be coupled to catheter 302 via a tubing. In some embodiments, irrigation pump 330 may allow for fluid to be pumped through the tubing and released at the tissue site through catheter 302 (e.g., through optical view ports or through separate irrigation slits at the distal section of catheter 302). Fluid from the irrigation pump 330 may cool the distal section of catheter 302 and the surrounding tissue during ablation, and also flush away any debris during and/or after ablation.

In some embodiments, catheter 302 may be coupled to console 310 via one or more optical connections 312 and one or more electrical connections 314. Optical connections 312 may include single mode optical fibers and/or multimode optical fibers that allow acquisition and/or transmission of optical signals to and from catheter 302 and console 310 for further analysis. Electrical connections 314 may include wiring, pins, and/or components used for supplying power and energy from signal generator 320 to catheter 302 for ablation.

In some embodiments, the optical and electrical connections 312, 314 may be connected to console 310 via a communication interface 316. Communication interface 316 may allow for transmission of various signals (e.g., optical and electrical signals) between catheter 302 and console 310. In some embodiments, the communication interface 316 may include a connector that facilitates proper alignment of optical fibers between the catheter 302 and console 310.

Exemplary Catheter Tip, Support Structure, and Optical Fiber Alignment Embodiments Disclosed herein are embodiments of an ablation catheter, including support structures and components for alignment of optical fibers in the distal section of the catheter. By providing such support structures, optical fibers and lenses may be properly aligned and secured in catheter tips to provide efficient optical data of measurements taken during and after ablation.

Figure 4A:
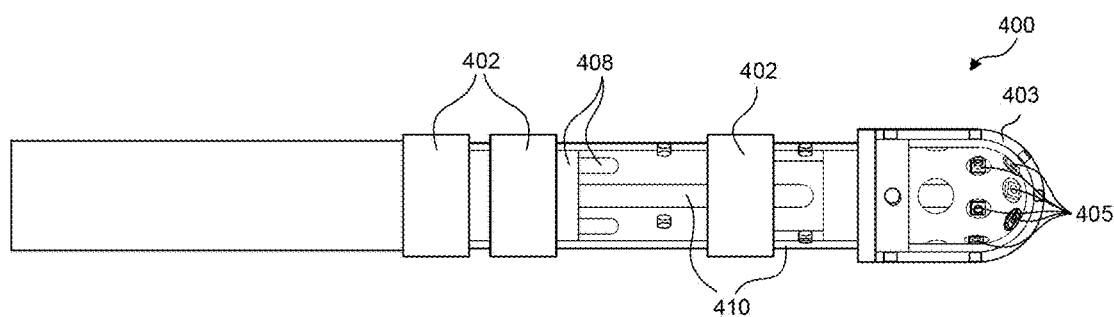
FIG. 4A illustrates a diagram of an example distal section of a catheter, according to embodiments of the present disclosure.

FIG. 4A illustrates a diagram of an example distal section of catheter 400, according to embodiments of the present disclosure. In some embodiments, the distal section of catheter 400 in FIG. 4A may represent an exemplary embodiment of distal section 104 of catheter 100 shown in FIG. 1. The distal section of catheter 400 includes a plurality of electrodes 402, ablation cap 403, a plurality of optical ports 405, one or more pull wire components 408, and irrigation tubing 410. In some embodiments, ablation cap 403 may also be an electrode and may be metallic. In some embodiments, ablation cap 403 may be referred to as a distal cap. In some embodiments, the plurality of optical ports 405 may be referred to herein as a plurality of optical view ports. In some embodiments, the pull wire components 408 may include an anchor and/or other components for allowing steering of the distal section of catheter 400 in order to maneuver within and target specific tissue regions for ablation. In some embodiments, irrigation tubing 410 may allow fluid to be guided along the catheter tip to cool tissue.

Figure 4B:
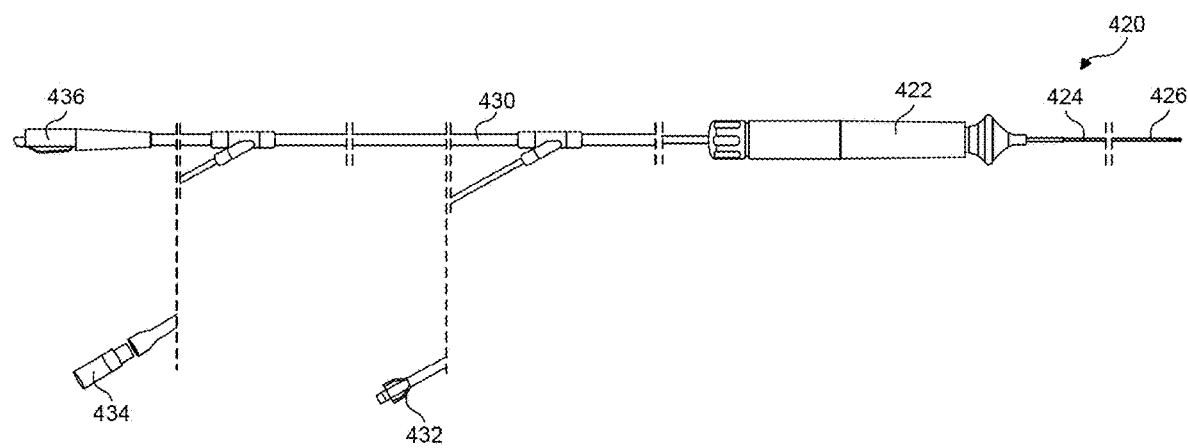
FIG. 4B illustrates a diagram of an example catheter, according to embodiments of the present disclosure.

FIG. 4B illustrates diagram of an example catheter 420, according to embodiments of the present disclosure. In some embodiments, catheter 420 in FIG. 4B may represent an exemplary embodiment of catheter 100 shown in FIG. 1 and the catheter shown in FIG. 4A. Catheter 420 includes handle assembly 422, shaft 424, tip 426, extension line 430, irrigation port 432, connector 434, and connector 436. In some embodiments, connector 434 may be used to connect an electronic device, such as a signal generator for generating energy for ablation (e.g., RF, cryogenic, or electroporation (e.g., pulsed electric field) signals), to the catheter 420. In some embodiments, connector 436 may be a multi-fiber connector that allows a plurality of optical fibers from the console (e.g., console 310) to be coupled to the catheter 420.

In some embodiments, the catheter of FIGS. 4A and 4B may have a single direction or multi-direction steerability. In order to allow for steerability, pull wires (e.g., pull wire components 408) may be connected to the distal section of the catheter (e.g., distal section of catheter 400) and controlled by the catheter's handle (e.g., handle 422). In some embodiments, a thermocouple, electrodes (e.g., electrodes 402), RF wires and an ablation cap (e.g., ablation cap 403) may be connected to the tip of the catheter (e.g., tip 426). In some embodiments, the ablation cap 403 may include multiple optical ports 405, which may serve as orifices for irrigation and also as optical windows or view ports for light beams from a plurality of optical fibers in the catheter.

In some embodiments, the optical fibers may be directed through the catheter shaft to lenses on the distal section of the catheter. In some embodiments, the optical fibers may be connected to the lenses by wafer-based wave-guide circuits that define the optical components at the catheter tip. In other embodiments, the optical fibers in the catheter tip may connect directly to the lenses, which focus the light into the tissue through the plurality of optical ports 405. In some embodiments, the lenses may be silicon or formed from another optically transparent material. In some embodiments, the lenses may also be coated to reduce reflections at interfaces or to allow optical index differences with surrounding tissue, blood, or fluid media.

In some embodiments, the catheter tip may include passive and fixed optics components (e.g., 15 fibers with 15 lenses attached), without any mechanical switching or scanning devices in the catheter itself. In some embodiments, movement or rotation of optical elements may allow for scanning in different directions in the tissue. In some embodiments, the plurality of optical ports or view ports in the catheter may have various orientations in the catheter tip, in which each output beam directed from each view port in the catheter may face a different direction. For example, one output beam may be directed forward, seven output beams may be directed at 45° with respect to tissue, and seven output beams may be directed at 90° with respect to tissue. In some embodiments, there may be any number of beams, view ports, orientations of the view ports in the catheter tip.

In order to provide precise alignment of the optical fibers with view ports in the catheter tip, disclosed herein are apparatuses, devices, and support structure embodiments for holding fibers and lenses in place at the proper locations in the plurality of view ports in the catheter tip. In some embodiments, a support structure may be provided in the catheter tip to hold optical fibers and corresponding lenses in proper locations and direct beams exiting the optical fibers in the appropriate directions. In some embodiments, the support structure may also help secure a cap (e.g., ablation cap 403) in place at the catheter tip and direct irrigation flow in the catheter. Additionally, the support structure, in some embodiments, may facilitate in the electrical conduction of energy from a generator wire (e.g., coupled through connector 434 for generating energy for ablation from a signal generator) to the cap of the catheter tip. In some embodiments, the support structure may include orifices also known as alignment orifices to hold the lenses in place, and measured tolerances between the alignment orifices and the lenses may ensure correct positioning. In some embodiments, the support structure may be electropolished or surface-treated to reduce friction, to allow easier threading of the optical fibers through alignment orifices during assembly.

In some embodiments, the support structure may be constructed from a single component or multiple components to facilitate assembly. In some embodiments, slits on the sides of the support structure may be used to increase the bending curvature of the fibers that direct the lenses, thus, reducing stress on the fibers themselves and stress at the lens-fiber interface resulting from bending torque. Additionally, in some embodiments, one or more mechanical features may be used to disassemble the different support structure components, fibers, lenses, and cap. In some embodiments, the lenses may be held in place by the cap to ensure alignment at the optical ports in the cap. In some embodiments, support structures constructed from two components may be aligned using the lenses themselves (e.g., via teeth in between the upper and lower components of the support structure/tip assembly).

Various support structure embodiments for holding fibers and lenses in place at the proper locations in the catheter tip are shown in the example diagrams of FIGS. 5-17.

Figure 5:
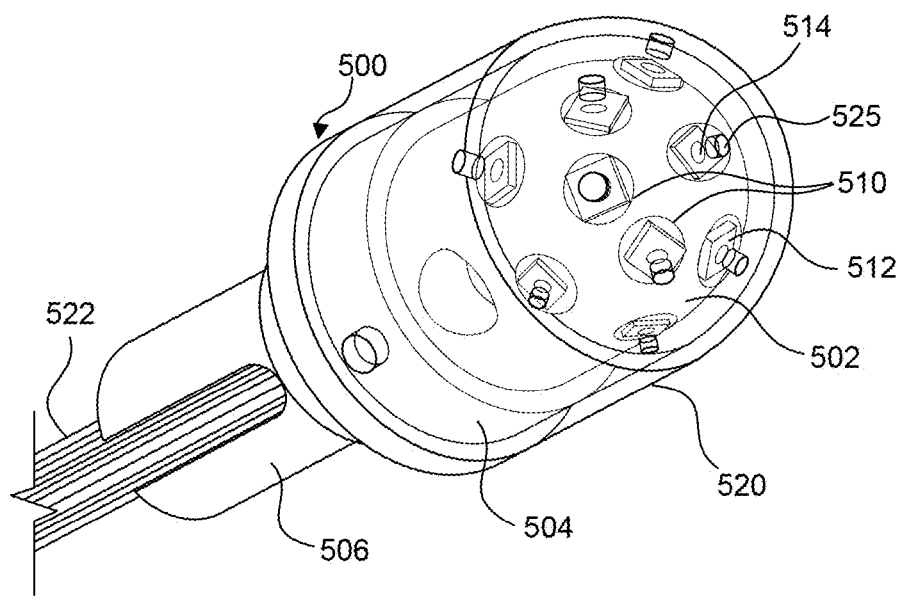
FIG. 5 illustrates a diagram of an example support structure, according to embodiments of the present disclosure.

FIG. 5 illustrates a diagram of an example support structure 500, according to embodiments of the present disclosure. Support structure 500 includes a distal end 502, a body 504, and proximal end 506. The distal end 502 includes a plurality of orifices 510, in which each orifice includes a corresponding optical fiber 512 of a plurality of optical fibers 512. In some embodiments, the plurality of orifices 510 may be referred to herein as alignment orifices or slits. In some embodiments, the plurality of optical fibers 512 may represent ends of the optical fibers. In some embodiments, optical fibers 522 may represent a bundle of optical fibers, from which the optical fiber ends 512 have been threaded through to each orifice 510. In some embodiments, the optical fiber ends 512 may be cleaved and polished before placement of corresponding lenses in a plurality of lenses 514 on each fiber end 512. In some embodiments, the plurality of lenses 514 may be affixed at each optical fiber end 512 using adhesive materials such as a glue, epoxy, or the like.

In some embodiments, a cap 520 may be attached over the distal end 502 of the support structure 500. The cap 520 may include a plurality of additional orifices 525. In some embodiments, locations of the additional orifices 525 may be aligned with locations of the plurality of lenses 514 attached to the ends of the optical fibers 512 in the orifices 510 in the distal end 502. In some embodiments, alignment of the orifices may allow for transmission of optical signals through the optical fibers 512 and lenses 514 to and from tissue, without interference from the support structure components/materials.

The support structure 500 may be assembled using different methods as described herein. In some embodiments, in a first method, the support structure 500 may be assembled by first attaching the lenses 514 to the ends of the optical fibers 512. The optical fibers 512 with the attached lenses 514 may then be affixed in the proximal end and then guided into the body 504 and distal end 506 of the support structure 500. In some embodiments, the proximal end 506 and body 504 may be a separate component from the distal end 502 and may be aligned and coupled together during assembly of the support structure 500.

In some embodiments, in a second method, the support structure 500 may be assembled by first threading the plurality of optical fibers 512 through the plurality of orifices 510 in the distal end 502 of the support structure 500. In some embodiments, the optical fibers 512 may be threaded from the distal end 502 through the body 504 and into the proximal end 506 of the support structure 500, and each optical fiber 512 may be threaded through a corresponding orifice in the plurality of orifices 510. An adhesive material may be applied at least partially at each orifice 510 in the distal end 502, such that the optical fibers 512 are fixed in place in the support structure 500. The plurality of optical fibers 512 may be cleaved (e.g., mechanical cleaving, laser cleaving, chemical cleaving) at the distal end 502 to remove portions of the optical fibers 512. The ends of the plurality of optical fibers 512 may be polished at the distal end 502. In an exemplary embodiment, when the distal ends of the optical fibers 512 are cleaved using a laser, such distal ends of the optical fibers 512 may not need a polishing step. Finally, a lens 514 may be attached to each of the ends of the plurality of optical fibers 512, resulting in a plurality of lenses 514 attached to the ends of the optical fibers 512 in the orifices 510 in the distal end 502.

In some embodiments, in order to stabilize the interface, a two-step fiber-lens gluing process may avoid the use of a ferrule, which may be expensive and time consuming for the polishing process. In some embodiments, the first glue section may use ultraviolet (UV) glue to obtain desired reflectivity/transmittance parameters. In some embodiments, the second glue section may comprise infrared (IR) curing for mechanical stability. In some embodiments, the shape may be properly controlled by the power, distance, and duration of the curing lamp, in order to avoid collision of lenses during the assembly process. In some embodiments, the two-step approach may ensure that the optical properties of the gluing connection are enhanced by using UV glue and that the light transmission from fiber to the lens (and vice versa) is as efficient as possible.

Figure 6:
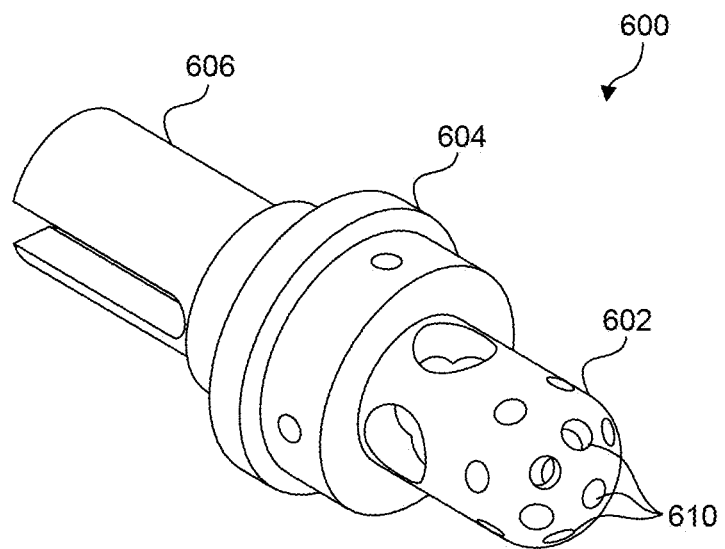
FIG. 6 illustrates a diagram of an example support structure with a unibody, according to embodiments of the present disclosure.

FIG. 6 illustrates diagram of an example support structure 600 with a unibody, according to embodiments of the present disclosure. In some embodiments, the support structure 600 shown in FIG. 6 may be manufactured as a single unibody component. In some embodiments, FIG. 6 illustrates the support structure 600 without any optical fibers or lenses attached for illustrative purposes. Support structure 600 may include a distal end 602, a body 604, and a proximal end 606. The distal end 602 may include a plurality of orifices 610. While only three orifices 610 are labeled for illustrative purposes, it is understood that there may be any number of orifices 610 in the distal end 602 of the support structure 600.

Figure 7:
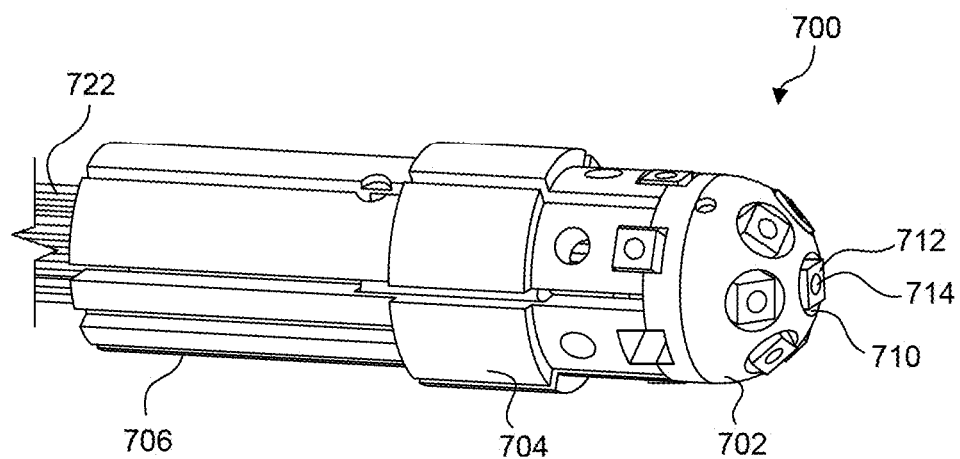
FIG. 7 illustrates a diagram of an example support structure without a cap attached, according to embodiments of the present disclosure.

FIG. 7 illustrates a diagram of an example support structure 700, according to embodiments of the present disclosure. Support structure 700 includes a distal end 702, a body 704, and proximal end 706. The distal end 702 includes a plurality of orifices 710, in which each orifice includes a corresponding optical fiber 712 of a plurality of optical fibers 712 and a lens in a plurality of lenses 714 affixed to each fiber end. In some embodiments, optical fibers 722 may represent a bundle of optical fibers, from which the optical fiber ends 712 have been threaded through to each orifice 710.

Figure 8:
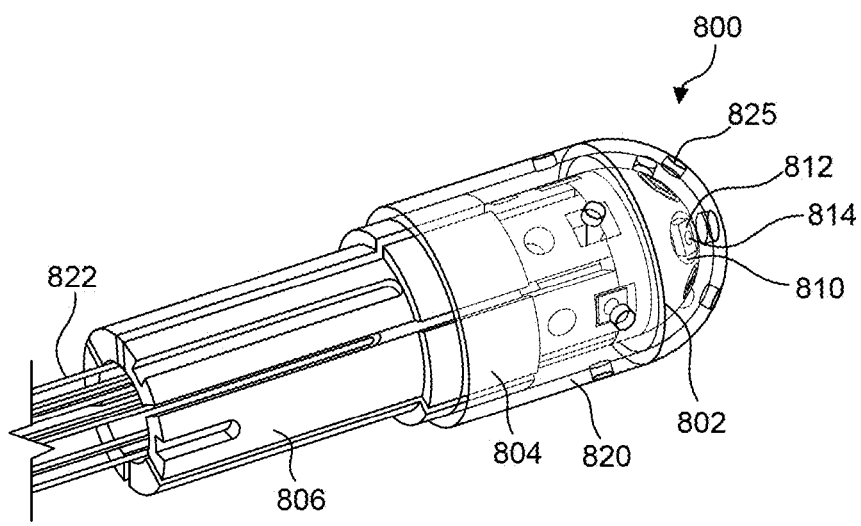
FIG. 8 illustrates a diagram of an example support structure, according to embodiments of the present disclosure.

FIG. 8 illustrates a diagram of an example support structure 800, according to embodiments of the present disclosure. Support structure 800 includes a distal end 802, a body 804, and proximal end 806. The distal end 802 includes a plurality of orifices 810, in which each orifice includes a corresponding optical fiber 812 of a plurality of optical fibers 812 and a lens in a plurality of lenses 814 affixed to each fiber end. In some embodiments, optical fibers 822 may represent a bundle of optical fibers, from which the optical fiber ends 812 have been threaded through to each orifice 810. In some embodiments, FIG. 8 also illustrates a cap 820 placed over the distal end 802 of the support structure 800, in which the cap includes additional orifices 825.

Figure 9:
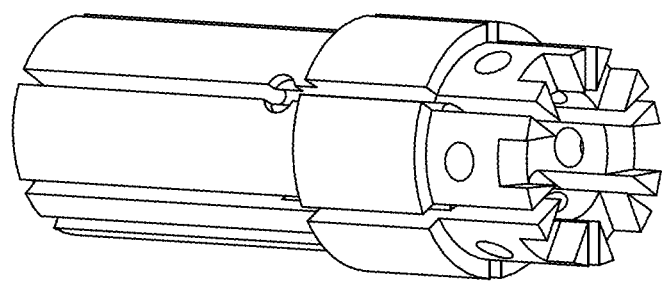
FIG. 9 illustrates a diagram of an example proximal end and body of the support structure, according to embodiments of the present disclosure.
Figure 10:
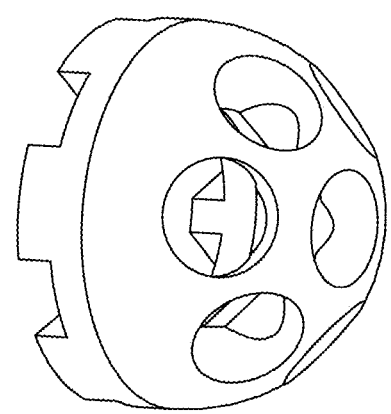
FIG. 10 illustrates a diagram of an example distal end of the support structure, according to embodiments of the present disclosure.

FIG. 9 illustrates a diagram of an example proximal end and body of the support structure, according to embodiments of the present disclosure. In some embodiments, the proximal end and body of the support structure may be manufactured as a separate component from the distal end of the support structure. FIG. 10 illustrates an example diagram of the distal end of the support structure, according to embodiments of the present disclosure. In some embodiments, the proximal end and body of the support structure of FIG. 9 may be aligned and coupled with the distal end of the support structure in FIG. 10.

Figure 11:
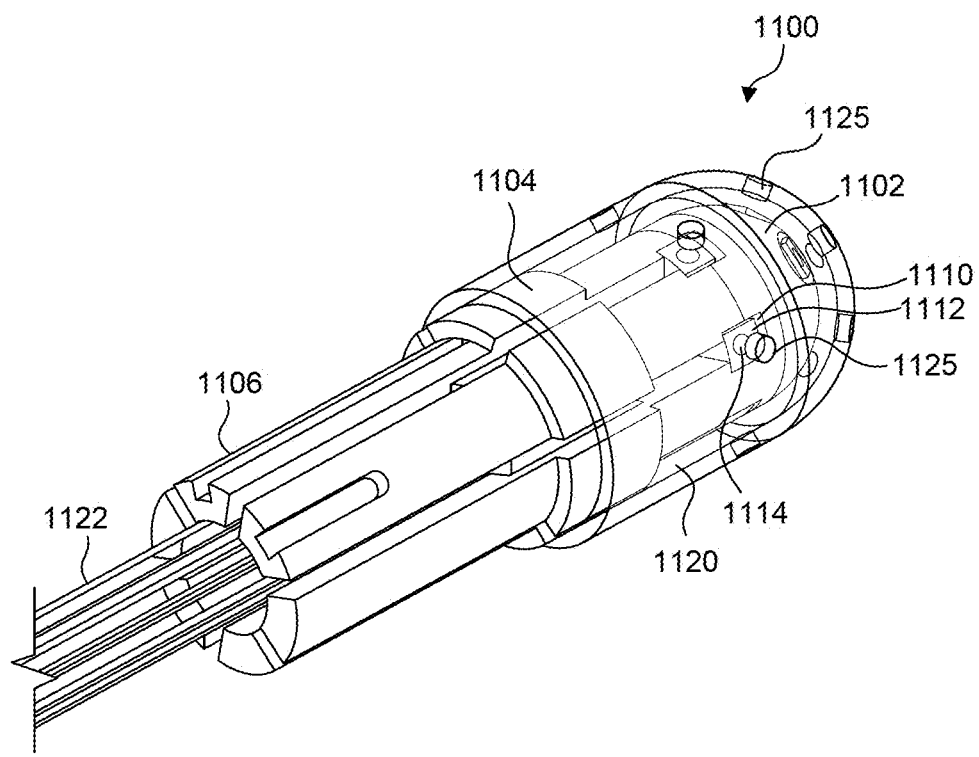
FIG. 11 illustrates a diagram of an example support structure, according to embodiments of the present disclosure.

FIG. 11 illustrates a diagram of an example support structure 1100, according to embodiments of the present disclosure. Support structure 1100 includes a distal end 1102, a body 1104, and proximal end 1106. The distal end 1102 includes a plurality of orifices 1110, in which each orifice includes a corresponding optical fiber 1112 of a plurality of optical fibers 1112 and a lens in a plurality of lenses 1114 affixed to each fiber end. In some embodiments, optical fibers 1122 may represent a bundle of optical fibers, from which the optical fiber ends 1112 have been threaded through to each orifice 1110. In some embodiments, FIG. 11 also illustrates a cap 1120 placed over the distal end 1102 of the support structure 1100, in which the cap includes additional orifices 1125.

In some embodiments, support structures 700, 800, and 1100 of FIGS. 7, 8, and 11, respectively, may represent exemplary embodiments of support structure 500 shown in FIG. 5. In some embodiments, FIGS. 5, 7, 8, and 11 illustrate different views and examples of the same support structure design. In some embodiments, FIG. 7 illustrates the example support structure without a cap, whereas FIGS. 5, 8, and 11 illustrate the cap affixed to the support structure.

Figure 12:
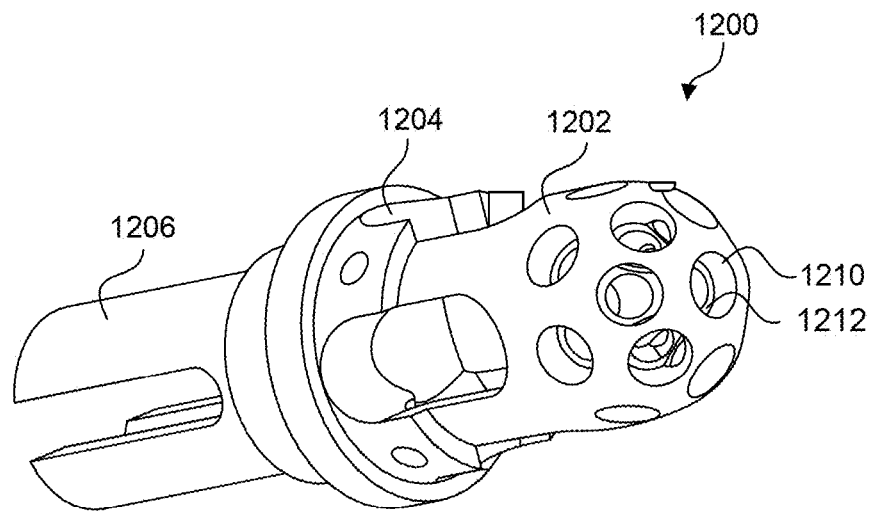
FIG. 12 illustrates a diagram of support structure with a unibody, according to embodiments of the present disclosure.

FIG. 12 illustrates a diagram of an example support structure 1200 with a unibody, according to embodiments of the present disclosure. In some embodiments, the support structure shown in FIG. 12 may have a plurality of orifices 1210 with a shoulder 1212 to accommodate holding lenses in place. In the configuration shown in FIG. 12, the support structure has multiple irrigation slits 1204.

Figure 13:
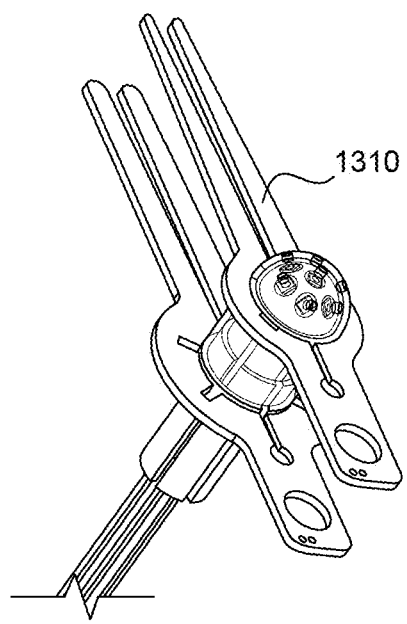
FIG. 13 illustrates a diagram of an example tool being used to couple or uncouple different components of a support structure together, according to embodiments of the present disclosure.

FIG. 13 illustrates a diagram of an example tool 1310 being used to couple or uncouple different components of a support structure together, according to embodiments of the present disclosure. In some embodiments, tool 1310 may be used to assemble and/or disassemble the distal end and body of the support structure together. In some embodiments, tool 1310 may be used to attach or detach the cap at the distal end of the support structure.

Figure 14:
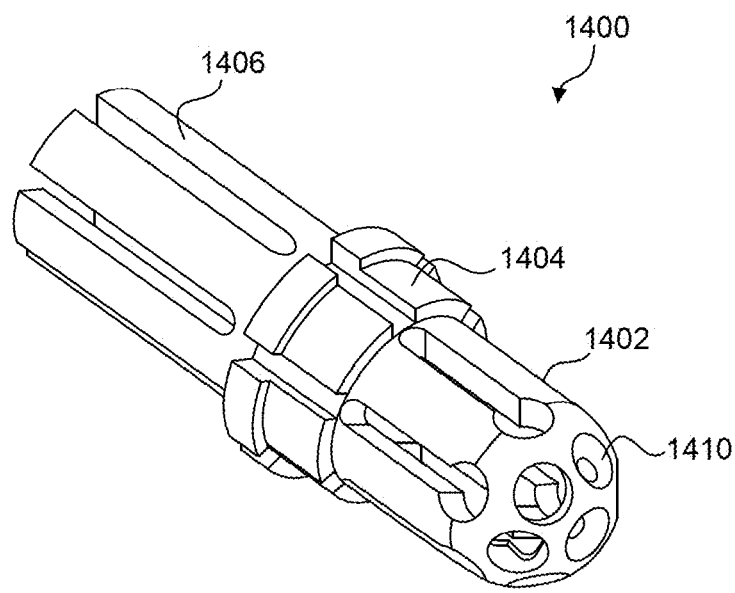
FIG. 14 illustrates a diagram of an example support structure, according to embodiments of the present disclosure.

FIG. 14 illustrates a diagram of an example support structure 1400, according to embodiments of the present disclosure. Support structure 1400 includes a distal end 1402, a body 1404, a proximal end 1406, and a plurality of concave orifices 1410 in the distal end 1402, to help align and hold in place a fiber-lens structure. FIG. 15 also illustrates an example diagram of a support structure 1500, according to embodiments of the present disclosure. Support structure 1500 includes a distal end with an indented surface 1502, a body 1504, a proximal end 1506, and a plurality of orifices 1510 in the distal end. The indented surface 1502 may be used as a site to engage a holding tool to be used during assembly. Similarly to the embodiments shown in FIGS. 6, 12, and 14, FIG. 15 also illustrates the support structure without any optical fibers or lenses assembled in the support structure.

FIGS. 16 and 17 illustrates a diagram of an example of a two-part support structure, wherein the inner support structure 1630 may be used to easily direct optical fibers 512. In some embodiments, inner support structure 1630 may be used to facilitate guidance and gluing of a plurality of optical fibers 512 and alignment of a cap 1120 (as shown in FIG. 11). In an exemplary embodiment, an outer support structure 1730 may be used to direct fibers adhered to the inner support structure 1630, in the direction of one of a plurality of orifices 510 or optical ports in a cap 1120.

FIGS. 18-21 illustrate diagrams of an example support structure during an assembly process, according to embodiments of the present disclosure. FIG. 18 illustrates a diagram of the distal end of the support structure. FIG. 19 illustrates a diagram of an example proximal end of the support structure, wherein the distal end and the proximal end of the support structure have corresponding orifices 1810 and 1910, respectively, to jointly receive a lens placed within such corresponding orifices, such that one or multiple lenses can serve as alignment surfaces when putting the distal and proximal ends of the support structure together during assembly.

FIG. 20 illustrates a diagram showing an example top view of the body of the support structure and the bending of optical fibers 522 after assembly. As shown in FIG. 20, fibers 522 may have a tendency to meet at the center of the support, generating a fiber knot 2000, which may be a high stress area. FIG. 21 illustrates a diagram showing an example orientation of optical fibers in the body and the proximal end of the support structure, wherein the support structure has relief slits 2110, in order to allow for the fibers to extend to the outside of the support body, and therein, allowing a larger radius of curvature of the bend of fibers to prevent fiber failure or breakage.

In some embodiments, the alignment of the distal end with the body and proximal end of the support structure may be feasible with a +/−20 um tolerance. As shown in FIGS. 18-21, the design may be constructed in two components in order to ease the assembly process and decrease the friction of optical fibers during the process. In some embodiments, the design may include slits 2110 around the body and/or proximal end of the support structure in order for 90-degree optical fibers to increase the curvature radii and minimize stress during bending of fibers. In some embodiments, the fibers may be placed and oriented in a dome-like shape that may act as strain relief during the final pulling of fibers. In some embodiments, this mechanism may be implemented in both proximal and distal sections of the support structure. In some embodiments, the slits 2110 in the support structure may ultimately facilitate fiber array placement.

In some embodiments, different lens designs or concepts may be used to facilitate with the assembly process. In some embodiments, wafer or MEMS-based designs may be utilized to increase the mechanical strength between lenses and fibers. FIG. 22 illustrates a diagram showing an example cross-sectional view of a wafer-based design for a lens arrangement, according to embodiments of the present disclosure. FIGS. 23 and 24 illustrates a diagram showing an example cross-sectional orthogonal views of a wafer-based design for a lens 514 and optical fiber arrangement 522, wherein the lens 514 incorporates an attachment reinforcement section 2310, a stabilizing area 2320, and a focusing area 2330. In this exemplary embodiment, the reinforcement section 2310 is used to guide the optical wire during assembly, augment the surface area for adhesion between the optical fiber 522, and the lens 514 (e.g., increasing strength of union), and stabilize the adhesive union when the fiber-lens assembly is subjected to bending or torsional loads. The stabilizing area 2320 serves to stabilize or hold in place the lens 514 within the support 500 structure while the focusing area 2320 is use to focus optical beams. FIG. 24 illustrates a diagram showing an example cross-sectional view of a wafer-level assembly of lenses, according to embodiments of the present disclosure. In some embodiments, FIG. 24 also illustrates the dicing locations at which the wafer may be cut.

In some embodiments, mirror or reflective surfaces may be added in the wafer-based lens designs. FIG. 25 illustrates a diagram showing an example cross-sectional view of a wafer-based design with a mirror or reflective surface 2510 to redirect the beams of light from the fiber 522, according to embodiments of the present disclosure. Such reflective surfaces 2510 may be manufactured by etching a silicon surface and adding a reflective coating. FIG. 26 and FIG. 27 also illustrate diagrams of example mirror or reflective surfaces 2510 on lenses added in different regions for wafer-based design, according to embodiments of the present disclosure. In some embodiments, mirror or reflective surfaces 2510 may be added directly to the optical fiber's 522 distal end in different directions to change the orientation of the light path from how the light travels in the fiber to when the light leaves the length of the fiber. In some embodiments, changing the light orientation may minimize the need for bending the fiber. By changing the angle of the etching in the silicon wafer, 90 degrees, 45 degrees, and forward-looking directions may be achieved within the same fiber orientation. In some embodiments, this concept may be reproduced to achieve any shape and/or orientation along the catheter tip.

In some embodiments, the support structure embodiments described herein may also include the design of silicon lenses with constructed geometries (e.g., slits, ledges, and lips) to fit well within the support structure to ease the lens-fiber assembly. FIGS. 28A-28D illustrate diagrams of example lens structures for attaching to fiber ends, according to embodiments of the present disclosure. In an exemplary embodiment a slit/channel in the lens design may be used as an adhesive overflow 2810, in order to allow for extra adhesive to flow easily outside of the adhesive union area. In some embodiments, fibers may be pre-polished flat to fit into the lens structures. In some embodiments, ledges, shoulders, channels or other geometrical features may be used as optical separation surfaces 2820 to allow for a controlled distance between the end of the optical fiber and the lens prior, during, or after adhesion. This may achieve a specific separation between the fiber and a bottom surface of the lens structure, allowing for controlled optical characteristics of the union and repeatability. In some embodiments, the optical separation surface 2820 may be filled with optical index matching resin, and may include a resin pocket (e.g., about 10 microns in height). In some embodiments, the lens structures may be built from silicon and be about 500 um in size. In some embodiments, anti-reflective (AR) coatings may be used on a lens surface, which may be optically coupled to the fiber and to the lens curvature itself, in order to minimize reflection from surrounding tissue or fluids.

FIGS. 29 and 30 illustrate diagrams showing example views of additional lens structures in a wafer design, according to embodiments of the present disclosure. In some embodiments, weak points or other rapid release features 2910 may be included in the wafer design to allow for a rapid release of the independent lenses from the wafer design.

FIG. 31 illustrates a diagram showing the example arrangement of the plurality of fibers with lenses and reflective surfaces, according to embodiments of the present disclosure. FIG. 32 illustrates a diagram showing example orifices for the fiber optics in the arrangement of the plurality of fibers with lenses and reflective surfaces, according to embodiments of the present disclosure. In some embodiments, silicone, glass, or other optically clear material structures may be etched, grown, printed, machined or manufactured to replace the distal tips of the fibers so that no bending (or excess fiber bending) is needed. In some embodiments, as shown in FIGS. 31 and 32, reflective surfaces may be added to redirect the light, and AR coating may be added to the lenses to control their refractive index and focal point. In some embodiments, single-core or multicore fibers may be connected to multi-lens systems using flip-chip bonding between them.

FIG. 33 illustrates a block diagram of an example multiple multiplexing light transmission structure. In some embodiments, optical circuits may be used to direct light into wafer-etched lenses 3310, and several multiplexers 3320 or beam splitters may be used to reduce the number of fibers that pass through the catheter shaft in some embodiments where flexible wafer-based waveguide circuits 3330 are used.

FIG. 34 illustrates a diagram of an example design in which light beams are directed to prevent bending of fibers or waveguides, according to embodiments of the present disclosure. As shown in FIG. 34, support structures may include designs, in which free-space optics and reflective surfaces are used to direct the beams of light without the need for bent fibers or waveguides.

In some embodiments, manufacturing and scaling of some of the embodiments described herein may be based on initially creating the fiber-lens assembly with an alignment that aims at minimizing reflections and maintains the specification of the focal length. In some embodiments, creating the fiber-lens assembly may be accomplished by active alignment using light passing through the fiber to align the lens or by adding mechanical features to the lens itself to passively align the corresponding fiber. The fiber-lens assembly may then be passed through the catheter tip, shaft or handle. In other exemplary embodiments, optical fibers may be passed through the tip, shaft, and handle prior to the creation of the fiber-lens assembly. During any or both of these assembly process options, passing the fiber or the fiber-lens assembly fully from one end to another of the shaft 106 through an axial channel may lead to damage/braking of the fiber or fiber-lens assembly. In some embodiments, in order to facilitate the passage of fibers, fiber-lens assemblies, wires, cables, rods, or any other element, through at least a section of the shaft during assembly, a two-part (e.g., insert, sheath) shaft design may be used to replace multichannel catheter extrusions. FIG. 35 illustrates a diagram showing a example of the two-part shaft structure composed of an external sheath 3510 and an internal insert 3520 with lateral slits 3530. The lateral slits 3530 can be used to insert one or multiple optical fibers, fiber-lens assemblies, or any other elongated element or elements from the side (e.g., radially as shown in the FIG. 35) without the need for pulling or pushing through axial channels. After elements are aligned within such slits, the sheath 3510 may be axially passed over (e.g., "rail-road over"), the insert 3520 and the aligned elements within the slits 3530 to create a shaft with channels/slits which have already been loaded with the desired elements. In some exemplary embodiments, the insert 3520 may also have radial channels for features such as the cooling channel.

In additional embodiments of the catheter assembly process, fibers may first be passed through the shaft and the tip support structure and then fixed in the appropriate directions. This shaft assembly may then be mounted on a fully automated or partially automated system. In some embodiments, the distal ends of the fibers may be cleaved mechanically, or by using a laser, and polished when needed (e.g., polishing might not be needed with laser cleaving) The proximal end of the fibers may then be connected to a light source to allow for the active alignment of the lenses. Lenses may be moved and located onto the support structure using an articulated arm that can be fully or partially automated. An adhesive material, such as glue or epoxy, may then be applied, and the lenses may be attached after active alignment is confirmed.

In some embodiments, additional support structure designs may be utilized, such as the design shown in FIGS. 36A-D. FIG. 36A illustrates a diagram of an example support structure design for the catheter tip, according to embodiments of the present disclosure. FIG. 36B illustrates a diagram of an example cross-section of the distal end of the support structure design shown in FIG. 36A, according to embodiments of the present disclosure. FIG. 36C illustrates a diagram of an example top view of the distal end of the support structure design shown in FIG. 36A, according to embodiments of the present disclosure. FIG. 36D illustrates a diagram of a cross-section of an example side view of the support structure design shown in FIG. 36A, according to embodiments of the present disclosure. In the exemplary embodiments of FIG. 36A, the support structure may have precise orifices 3610 designed to tightly fit an optical fiber that passes through. In some embodiments, the manufacturing tolerance of such orifices 3610 may be within +/−10 microns of desired nominal diameter.

In some embodiments, FIGS. 36A-D may illustrate examples of the constructed support structure, which may be made of a biocompatible metal (e.g., stainless steel, titanium alloys, nickel alloys, platinum, platinum alloys, etc.), glass or biocompatible polymer or ceramic. In exemplary embodiments, the support structure is treated after initial manufacture to achieve a smooth surface finish and remove sharp edges independent of the material used. In some embodiments, stainless steel may be used to manufacture the support structure with an electropolished surface finish. Electropolishing may be used to simplify the passage of the optical fibers which tightly fit through the precise orifices 3610 and remove sharpness from the edges to reduce the risk of fracture of such fibers. FIG. 36D further illustrates a cross-section of the full support structure design. In some embodiments, the support structure may include a distal end, a body, and a proximal end as illustrated in other support structure embodiments described herein. In some embodiments, the support structure shown in FIG. 36A may be a unibody design. In FIG. 36B, the cross-section of the distal end shows a plurality of precise orifices 3610, in which optical fibers may be threaded through. Furthermore, the support structure design shown in FIG. 36C illustrates the plurality of precise orifices 3610 from the top view. The support structure illustrated in FIGS. 36A-D may also be configured to have adhesive channels 3620, recessed from the structure's surface to allow adhesive to at least fill partially such channels 3620 to improve fixation, allow for better polishing without interference from metal particles disposed over the core of the optical fiber, and optical access for laser cleaving before adhesion of the fiber or optical access to use light-setting adhesives when attaching the lenses to the fibers.

FIG. 37A illustrates a diagram of an example fiber alignment tool 3730 arranged in a distal end of support structure 3700, wherein optical fiber alignment slits 3710 are used instead of precise orifices 3610 to hold the fibers in place. The use of fiber alignment slits 3710 instead of precise orifices 3610 may allow for easier and faster threading of each fiber which can then be bended in place within the slit and fixed at the correct location using adhesives or mechanical interference from another element brought into the slit from the distal end of the support structure. In some embodiments, a fiber alignment tool 3730 may be inserted in the distal end of support structure 3700 to facilitate guidance and gluing of a plurality of optical fibers in the distal end.

FIGS. 37B-C illustrate diagrams of the cross-sectional view of slit patterns that may be used as part of the fiber alignment tool 3730 to organize, direct and hold fibers in place during the assembly process. In some embodiments, tool 3730 may guide each fiber into alignment at the proper locations corresponding to orifices or slits in the distal end of a support structure.

In some embodiments, optical fibers may be threaded from the proximal end of the support structure to the distal end of the support structure, and then subsequently glued at the orifices or slits of the distal end of the support structure. In some embodiments, optical fibers may be threaded from the distal end of the support structure to the proximal end of the support structure and then subsequently glued at the orifices or slits of the distal end of the support structure. FIG. 37D illustrates a diagram of a distal end of a support structure with fiber alignment slits 3710, which allow for threading of the optical fiber 522 in both directions, distal to proximal and proximal to distal.

FIG. 37E illustrates an additional diagram showing the example arrangement of optical fibers 3712 in the support structure 3700, according to embodiments of the present disclosure. In some embodiments, a plurality of optical fibers 3712 may be oriented through slits on the sides of the support structure 3700 and threaded through a plurality of precise orifices 3610 in the distal end of the support structure 3700, wherein a thinner section 3713 allows for the optical fibers 3712 to be externalized easily due to the orientation of the precise orifices and the geometry of the distal section. Optical fibers that are external to the orifice may have a higher bending radius, resulting in less stress and less risk of failure. Additionally, the thinner section 3713 and the direction of the precise orifices 3610 may allow for the fibers 3712 to be threaded through the precise orifices 3610 either from the proximal end to the distal end of the support structure, or from the distal end to the proximal end of the support structure with ease.

FIG. 38A illustrates a diagram showing the example arrangement of optical fibers 3812 in the support structure 3800, according to embodiments of the present disclosure. In some embodiments, a plurality of optical fibers 3812 may be threaded through the body of the support structure 3800 and out a plurality of orifices 3810 at the distal end of the support structure 3800.

In some embodiments, the support structure 3800 may include one or more slits/orifices 3835, through which the fibers may be arranged. In some embodiments, the one or more slits 3835 may facilitate the threading of the optical fibers 3812 and reduce their bending curvature, while also serving as paths for irrigation and cooling fluids. In some embodiments, adhesive channels 3620 may be filled with epoxy or glue in order to prevent particles or metal from interfering with the fibers 3812. In some embodiments, the one or more adhesive channels 3620, prior to being filled with adhesives, may also facilitate cleaving of the fibers 3812 with a laser. For example, the fibers 3812 may be cleaved by using an automated laser, in which a laser beam may go through the one or more adhesive channels 3620 to cleave the fibers 3812 laterally. In some embodiments, the one or more slits 3835 may be offset on the sides of the distal end of the support structure 3800 to facilitate the placement of fibers inside and prevent fibers from colliding with each other and interfering with fiber pathways.

FIG. 38B illustrates a diagram of an example top view of the distal end of the support structure, according to embodiments of the present disclosure. The diagram in FIG. 38B shows a plurality of orifices 3810 at which the plurality of optical fibers may be threaded through. In some embodiments, after being threaded through the orifices 3810, the ends of the optical fibers may be cleaved, glued, and polished, prior to attaching lenses.

FIG. 38C illustrates a diagram of an example side view of the distal end of the support structure after arrangement, cleaving, gluing, and polishing of the fibers within support structure, according to embodiments of the present disclosure. In exemplary embodiments, the precise orifices 3610 or fiber alignment slits 3710 may be offset in the axial radial direction "R" and/or in the axial direction "A" with respect to each other. Since the position of the precise orifices 3610 or fiber alignment slits 3710 determines the position of the lenses 3870 and the optical fibers 3812 within the support body, such offsets allows for easier threading of the fibers, since the fiber ends will not be directed to a same center, and thus may or may not generate a smaller fiber knot 2000. FIG. 38D illustrates a diagram of an example support structure, wherein the precise orifices 3610 are angled/aligned, so that the optical fibers 3812 are not directed to a common center when being threaded in the support structure to reduce the probability of a size of a fiber knot 2000.

FIG. 38E illustrates a diagram of an example support structure with lenses attached, according to embodiments of the present disclosure. In some embodiments, a plurality of lenses may be affixed at each optical fiber end on the surface of the support structure after cleaving, gluing, and polishing of the fibers. In some embodiments, the plurality of lenses may be affixed at each optical fiber end using adhesive materials such as a glue, epoxy, or the like. In the example illustrated in FIG. 38E, the precise orifices 3610 or alignment slits 3710 for the fibers attached to the 45 degree distal lenses 3814 are offset or angled differently relative to each other as not to cause a fiber knot 2000 at the 45 degree lens level.

FIG. 38F illustrates a diagram showing an example two-part support structure with lenses attached, according to embodiments of the present disclosure. FIG. 38F shows the plurality of lenses 3814 at each optical fiber end in the distal body 3820 of the support structure, and a plurality of lenses at the interface between the distal body 3820 and proximal body 3826 of the support structure. In this hybrid two-part embodiment, the 45 degree lenses 3814 on the distal body 3820 and the lenses at the interface between the distal and proximal bodies are glued place using gluing slits 3824. The central lens 3880 is aligned in free space, and then glued in place using a drop of resin or adhesive.

Exemplary Method Embodiments

In some embodiments, the catheters, support structures, and components described herein may be manufactured and assembled to align and secure optical fibers in place at catheter tips for use in tissue ablation procedures. In some embodiments, the optical fibers and lenses in the support structure may be affixed in the catheter tip using various methods, as described herein.

FIG. 39 illustrates an example method 3900 for assembling a plurality of optical fibers and lenses in a support structure for an ablation catheter, according to embodiments of the present disclosure. In some embodiments, method 3900 may be performed to assemble the various support structure embodiments as described herein.

At block 3902, a unibody support structure comprising guiding orifices or slits for optical fiber alignment is provided. In some embodiments, the orifices or slits may determine the positioning of the optical fibers and/or lenses in the distal end.

At block 3904, a plurality of optical fibers may be threaded through the plurality of orifices or slits at the distal end of the support structure. In some embodiments, the optical fibers may be threaded from the distal end through the body and into the proximal end of the support structure. In some embodiments, the optical fibers may be threaded from the proximal end through the body to the distal end of the support structure through the orifices or slits.

At block 3906, an adhesive material may be applied so that all of the optical fibers are fixed in place in the support structure. In some embodiments, the adhesive material may be a glue, an epoxy, or the like. In some embodiments, the adhesive material may help stabilize the optical fibers in the support structure and prevent movement of the fibers.

At block 3908, the plurality of optical fibers may be cleaved at the distal end to remove portions of the optical fibers extending out of the distal end of the support structure.

At block 3910, ends of the plurality of optical fibers may be polished at the distal end. In some embodiments, the fiber ends may be polished at the distal end surface to remove any excess glue remaining on the fiber end surfaces at the distal end. In some embodiments where fibers are cleaved using a laser or other precise mechanical means, the polishing step of the fiber surfaces might not be included.

At block 3912, a lens may be attached to each of the ends of the plurality of optical fibers, resulting in a plurality of lenses attached to the ends of the optical fibers and fixed to the support structure. In some embodiments, the plurality of lenses may be permanently fixed to the support structure.

At block 3914, a cap containing a series of optical ports may be attached to the support structure, allowing for the optical ports in the cap to be optically aligned to the lenses attached to the support structure. In some exemplary embodiments, a cap might not be included, or the support structure and cap may be one of the same (e.g., as direct lens-tissue contact may be necessary). In such embodiments, the manufacturing method step in block 3914 might not be included.

FIG. 40 illustrates additional steps beyond those described in method 3900, in which the additional steps may be implemented for assembling a plurality of optical fibers and lenses in a two-part/body support structure for an ablation catheter, according to embodiments of the present disclosure. In some embodiments, the additional steps in method 4000 may be performed to assemble the various support structure embodiments as described herein.

At block 4002, one or multiple lens-fiber assemblies are attached to each of their corresponding positions in a proximal or distal body of a two-part support structure.

At block 4004, the positioning of the lenses on each of the two parts of the support structure is used to align the bodies of the two parts. In some embodiments, the two parts of the support body are moved so that they are in direct contact with each other while maintaining the alignment.

At block 4006, the distal and proximal bodies of the support structure are bonded or welded together. in some embodiments, bonding may be applying an adhesive material, such as a glue, an epoxy, resin or the like. In some embodiments, welding may be accomplished through a laser, a tungsten inert gas (TIG) welding system, or a metal inert gas (MIG) welding system, or other method.

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present disclosure and the appended claims in any way.

Embodiments of the present disclosure have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

Furthermore, the following aspects are explicitly disclosed:

1. A method for assembling a plurality of optical fibers and lenses in a support structure for an ablation catheter, the method comprising:
   providing a support structure comprising a proximal end, a body, and a distal end, wherein the distal end comprises a plurality of alignment orifices;
   threading a plurality of optical fibers through the plurality of alignment orifices at the distal end, wherein each optical fiber in the plurality of optical fibers is threaded through a corresponding alignment orifice in the plurality of alignment orifices;
   applying an adhesive material to the plurality of optical fibers and to the distal end, such that the plurality of optical fibers are fixed in place in the support structure;
   cleaving the plurality of optical fibers at the distal end to remove portions of the optical fibers extending out of the distal end of the support structure;
   attaching a lens to each of the ends of the plurality of optical fibers, resulting in a plurality of lenses attached to the ends of the optical fibers.

2. The method of aspect 1, wherein the alignment orifices are located at different radial locations in the distal end of the support structure.

3. The method of aspect 1 or aspect 2, wherein the plurality of optical fibers are threaded through the plurality of alignment orifices using a guiding tool to position each optical fiber at the corresponding optical port.

4. The method of one of the preceding aspects, further comprising: attaching a cap over the distal end of the support structure.

5. The method of aspect 4, wherein the cap comprises a plurality of optical ports, wherein locations of the plurality of optical ports are aligned with locations of the plurality of lenses attached to the ends of the optical fibers in the alignment orifices in the distal end.

6. The method of aspect 5, further comprising:
assembling the support structure in a distal section of an ablation catheter, wherein the distal end of the support structure with the cap is configured to interface with a portion of tissue.

7. A catheter comprising:
a proximal section;
a distal section;
a shaft coupled between the proximal section and the distal section, and
a plurality of optical fibers extending through the shaft and to the distal section of the catheter, wherein the distal section comprises:
a support structure comprising:
a proximal end;
a body; and
a distal end comprising:
a plurality of alignment orifices, wherein each optical fiber in the plurality of optical fibers is threaded through a corresponding alignment orifice; and
a plurality of lenses, wherein each lens is coupled to an end of a corresponding optical fiber in the plurality of optical fibers and located at the corresponding alignment orifice; and
a cap positioned over a portion of the distal end of the support structure, wherein the cap comprises a plurality of optical ports, wherein locations of the plurality of optical ports are aligned with locations of the plurality of lenses in the plurality of alignment orifices, and
wherein the support structure is configured to hold the plurality of optical fibers in place and align each optical fiber with the corresponding alignment orifice in the plurality of alignment orifices.

8. The catheter of aspect 7, wherein the optical fibers are fixed in place by an adhesive material applied at each alignment orifice in the distal end of the support structure.

9. The catheter of aspect 7 or aspect 8, the alignment orifices are located at different radial locations in the distal end of the support structure.

10. The catheter of one of aspects 7 to 9, wherein each optical fiber is threaded through the corresponding alignment orifice using a guiding tool to position each optical fiber at the corresponding alignment orifice.

11. The catheter of one of aspects 7 to 10, wherein the plurality of alignment orifices and the plurality of optical ports are configured such that each optical fiber and corresponding lens face out in a different direction and/or angle.

12. The catheter of one of aspects 7 to 11, wherein the support structure is a unibody.

13. The catheter of one of aspects 7 to 12, wherein the support structure comprises two components assembled together.

14. The catheter of one of aspects 7 to 13, wherein the plurality of optical fibers comprises 15 optical fibers, and the plurality of lenses comprises 15 lenses.

15. A support structure for an ablation catheter comprising:
a proximal end;
a body; and
a distal end comprising a plurality of alignment orifices, wherein:
each optical fiber in a plurality of optical fibers is threaded through a corresponding optical port in the plurality of alignment orifice, and
each lens in a plurality of lenses is coupled to an end of a corresponding optical fiber in the plurality of optical fibers, resulting in a plurality of lenses, each lens being located at the corresponding alignment orifice; and
a cap positioned over a portion of the distal end of the support structure, wherein: the cap comprises a plurality of optical ports, and
locations of the plurality of optical ports are aligned with locations of the plurality of lenses in the plurality of alignment orifices, and
wherein the support structure is configured to hold the plurality of optical fibers in place and align each optical fiber with the corresponding alignment orifice in the plurality of alignment orifices.

16. The support structure of aspect 15, wherein the alignment orifices are located at different radial locations in the distal end of the support structure.

17. The support structure of aspect 15 or aspect 16, wherein the optical fibers are fixed in place by an adhesive material applied at each alignment orifice in the distal end of the support structure.

18. The support structure of one of aspects 15 to 17, wherein each optical fiber is threaded through the corresponding alignment orifice using a guiding tool to position each optical fiber at the corresponding alignment orifice.

19. The support structure of one of aspects 15 to 18, wherein the plurality of alignment orifices and the plurality of optical ports are configured such that each optical fiber and corresponding lens face out in a different direction and/or angle.

20. The support structure of one of aspects 15 to 19, wherein the plurality of optical fibers comprises 15 optical fibers, and the plurality of lenses comprises 15 lenses.

What is claimed is:

1. A method for assembling a plurality of optical fibers and a plurality of lenses in a support structure for an ablation catheter, the method comprising:
providing the support structure comprising a proximal end, a body, and a distal end, wherein the distal end comprises a plurality of alignment orifices;
threading the plurality of optical fibers through the plurality of alignment orifices at the distal end, wherein each optical fiber in the plurality of optical fibers is threaded through a corresponding alignment orifice in the plurality of alignment orifices;
applying an adhesive material to the plurality of optical fibers and to the distal end, such that the plurality of optical fibers are fixed in place in the support structure;
cleaving the plurality of optical fibers at the distal end to remove portions of the plurality of optical fibers extending out of the distal end of the support structure; and
attaching a lens to each end of the plurality of optical fibers, resulting in the plurality of lenses being attached to the ends of the plurality of optical fibers.

2. The method of claim 1, wherein the alignment orifices are located at different radial locations in the distal end of the support structure.

3. The method of claim 1, wherein the plurality of optical fibers are threaded through the plurality of alignment orifices using a guiding tool to position each optical fiber at a corresponding optical port.

4. The method of claim 1, further comprising: attaching a cap over the distal end of the support structure.

5. The method of claim 4, wherein the cap comprises a plurality of optical ports, wherein locations of the plurality of optical ports are aligned with locations of the plurality of lenses attached to the ends of the plurality of optical fibers in the alignment orifices in the distal end.

6. The method of claim 5, further comprising:
assembling the support structure in a distal section of the ablation catheter, wherein the distal end of the support structure with the cap is configured to interface with a portion of tissue.

\* \* \* \* \*